(12) United States Patent
Kriegel et al.

(10) Patent No.: US 9,778,243 B2
(45) Date of Patent: Oct. 3, 2017

(54) METHODS FOR MEASURING RENEWABLE BIO-SOURCE CONTENT IN RENEWABLE BIOPLASTIC MATERIALS

(75) Inventors: Robert Kriegel, Decatur, GA (US); Sheng Sheng Yang, Marietta, GA (US); Hsiao Hua Liu, Atlanta, GA (US); Christopher Mubarak, Cumming, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 13/235,330

(22) Filed: Sep. 16, 2011

(65) Prior Publication Data

US 2012/0322159 A1   Dec. 20, 2012

Related U.S. Application Data

(60) Provisional application No. 61/496,990, filed on Jun. 14, 2011.

(51) Int. Cl.
| | |
|---|---|
| *G01N 23/00* | (2006.01) |
| *G01N 33/44* | (2006.01) |
| *G01N 21/39* | (2006.01) |
| *H01J 49/00* | (2006.01) |

(52) U.S. Cl.
CPC ........... *G01N 33/442* (2013.01); *G01N 21/39* (2013.01); *H01J 49/0086* (2013.01)

(58) Field of Classification Search
None
See application file for complete search history.

(56) References Cited

U.S. PATENT DOCUMENTS

| | | |
|---|---|---|
| 2008/0103339 A1 | 5/2008 | Bloom |
| 2009/0246430 A1* | 10/2009 | Kriegel et al. ............... 428/36.6 |
| 2010/0168371 A1 | 7/2010 | Berti et al. |

FOREIGN PATENT DOCUMENTS

| | | | | |
|---|---|---|---|---|
| WO | WO 2010/005525 | * | 1/2010 | ............... C12P 5/02 |

OTHER PUBLICATIONS

Chico State University, Postconsumer Resin Quality Assurance and Testing Protocol, 2005, Contractor's Report to the Board, retrieved from internet: http://www.calrecycle.ca.gov/Publications/Documents/Plastics%5C43205003.pdf.*
Crosson et al., "A Stable Isotope Ratios Using Cavity Ring-Down Spectroscopy: Determination of 13C/12C for Carbon Dioxide in Human Breat?" *Analytical Chemistry*, vol. 74, No. 9 (2002).
"ASTM D6866-08 Standard Test Methods for Determining the Biobased Content of Solid, Liquid, and Gaseous Samples Using Radiocarbon Analysis" http://www.astm.org/Standards.D6866.htm (2010).
International Preliminary Report on Patentability for PCT/US2012/042245, dated Dec. 17, 2013.

* cited by examiner

*Primary Examiner* — Robert Xu
(74) *Attorney, Agent, or Firm* — King & Spalding

(57) ABSTRACT

The present invention relates to improved methods for measuring the renewable bio-source carbon content and renewable bio-content in renewable bioplastic resins produced in manufacturing plants. In particular, the present invention relates to measuring the renewable bio-source carbon content in renewable bioplastic resins produced during a production run by correlating measured $\delta^{13}C$ values are measured by iTOC-CRDS and CM-CRDS with actual renewable bio-source carbon content measurements (AMS or LSC $^{14}C$) via a linear regression.

11 Claims, 12 Drawing Sheets

METHODS FOR MEASURING RENEWABLE BIO-SOURCE CONTENT IN RENEWABLE BIOPLASTIC MATERIALS

CROSS REFERENCE TO RELATED APPLICATIONS

This application is a claims priority to U.S. Provisional Patent Application No. 61/496,990, filed Jun. 14, 2011. The complete disclosure of the above-identified application is fully incorporated herein by reference.

FIELD OF THE INVENTION

The present invention relates to methods of measuring the renewable bio-contents or renewable bio-source carbon contents in renewable bioplastic materials.

BACKGROUND

Conventional plastics are polymers made from monomeric materials derived from non-renewable petroleum and/or natural gas (petroleum-based-plastics or p-plastics). The identity of the particular plastic is characterized by the component monomers. Common plastics include, for example, polyethylene terephthalate (PET), polyethylene (PE), polypropylene (PP), polystyrene (PS), nylon, polycarbonate (PC), polyvinyl chloride (PVC), etc. PET is formed primarily from monoethylene glycol (MEG) and terephthalic acid (TA) (Scheme 1) and is widely used in bottles and containers for food and beverage products.

Scheme 1. Preparation of PET from TA and MEG

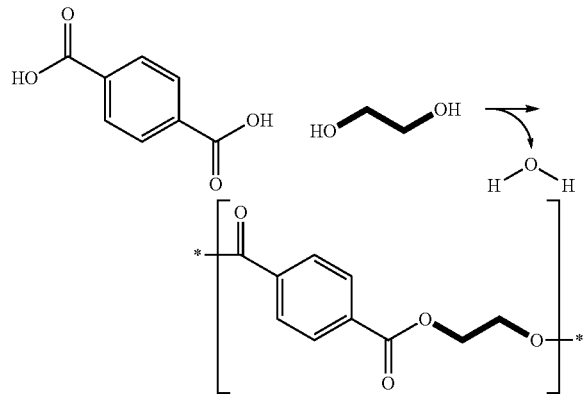

Non-renewable petroleum-based plastics have come under scrutiny for their environmental profile, including their role in contributing to greenhouse emissions and their "non-renewable" nature, meaning that they cannot be re-made, re-grown, or regenerated at a rate comparable to consumption. Non-renewable petroleum is made from oil which takes millions of years to form. The cost of non-renewable petroleum-derived plastics, which is closely tied to the rising cost of non-renewable petroleum, has also proven to be a negative for many users.

The problems posed by traditional plastics have led to the search for alternative materials. Renewable bio-based plastics or renewable bioplastics represent a new class of plastics made from renewable bio-mass source materials. These materials may include food or non-food crops including, for example, corn, rice, soy, or other sugar and starch-producing plants. A given plastic may be formed partially or fully from renewable bio-derived materials. Renewable bio-based PET, for example, can be made from renewable bio-derived monoethylene glycol (b-MEG) and non-renewable petroleum-derived terephthalic acid (p-TA). As a group, renewable bioplastics offer environmental advantages compared to non-renewable petroleum-based plastics, including a more limited reduced impact of greenhouse gas emissions and renewability.

Renewable bio-based plastics, such as renewable bio-based PET, can be produced using the existing manufacturing technology, more often than not using the same reactors and machinery. As a producer transitions from manufacturing petroleum-based plastics to renewable bioplastics, the non-renewable petroleum-derived starting materials are replaced with renewable bio-derived starting materials (or visa versa). During the transition, a mix of non-renewable petroleum-derived and renewable bio-derived materials are present. This mixing leads to the need for measuring renewable bio-content of the renewable bioplastic product.

Any product that contains some amount of renewable bio-based material within it is technically a renewable bio-based product. However, a certain minimum renewable bio-content is characteristic of materials labeled as renewable bio-plastics. A renewable bio-based PET resin made of renewable bio-derived monoethylene glycol (renewable bio-MEG) and non-renewable petroleum-derived terephthalic acid (p-TA) may contain up to about 30% renewable bio-content.

It is possible to determine the amount of carbon in a product that is derived from renewable bio-based materials relative to the total amount of carbon in the entire product. This is because renewable biomass contains a well-characterized amount of carbon-14 that is easily differentiated from other materials, such as fossil fuels, that do not contain any carbon-14. The percentage of a given product that is derived from renewable bio-based materials is generally measured by Accelerator Mass Spectrometry (AMS) or Liquid Scintillation Counters (LSC). LSC is generally considered relatively low precision and requires extensive sample preparation as well as long counting times that can take from days to weeks. AMS provides higher precision, but the capital and operating costs are high. In addition, processing time for third party vendor analysis of AMS can be long.

Thus, there is a need for a method to measure the renewable bio-source carbon content of a renewable bioplastic resin manufactured in a production facility efficiently and cost-effectively. In particular, in order to optimize the manufacturing process such that the maximum amount of renewable bio-material can be produced; there is a need to quickly and reliably measure the renewable bio-source carbon content of a renewable bioplastic resin manufactured in a production facility over time, particularly during transition periods in the process where non-renewable petroleum-derived plastic starting materials are swapped out for renewable bio-derived plastic starting materials.

Other objects, features, and advantages of this invention will be apparent from the following detailed description, drawings, and claims.

SUMMARY OF THE INVENTION

The present invention is directed to methods for measuring the renewable bio-content, or the renewable bio-source carbon content, in renewable bioplastics, including renewable bioplastic resins.

In one embodiment, the present invention is a method to measure the renewable bio-source content, or renewable bio-content, of a renewable bioplastic resin produced in a production plant over time (e.g. in a production run), which method includes:
 a.) measuring delta carbon-13 ($\delta^{13}C$) values of the renewable bioplastic resin samples throughout a production run;
 b.) determining the actual renewable bio-source carbon content of two renewable bioplastic samples in step a.) with the lowest and the highest $\delta^{13}C$ value;
 c.) correlating the $\delta^{13}C$ values in step a.) with the actual renewable bio-source carbon content of step b.) for the two resin samples;
 d.) determining indirectly the renewable bio-source carbon content of the remaining resin samples in the production run based on said correlation; and
 e.) calculating the renewable bio-content from the renewable bio-source carbon content.

In one embodiment, the present invention is a method to measure the renewable bio-source content, or renewable bio-content, of a renewable bioplastic resin produced in a production plant over time (e.g. in a production run), which method includes:
 a.) measuring delta carbon-13 ($\delta^{13}C$) values of at least two of the renewable bioplastic resin samples throughout a production run;
 b.) determining the actual renewable bio-source carbon content of the two renewable bioplastic samples in step a.) with the lowest and the highest $\delta^{13}C$ value;
 c.) correlating the $\delta^{13}C$ values in step a.) with the actual renewable bio-source carbon content of step b.) for the two resin samples;
 d.) determining the renewable bio-source carbon content of the remaining resin samples in the production run based on said correlation; and
 e.) calculating the renewable bio-content from the renewable bio-source carbon content.

In another embodiment, the present invention is a method to measure the renewable bio-source content, or renewable bio-content, of a renewable bioplastic resin produced in a production plant over time (e.g. in a production run), which method includes:
 a.) measuring delta carbon-13 ($\delta^{13}C$) values of at least one renewable bioplastic resin samples throughout a production run;
 b.) determining the actual renewable bio-source carbon content of the renewable bioplastic sample in step a.) or the renewable bioplastic sample in step a.) with the highest $\delta^{13}C$ value;
 c.) correlating the $\delta^{13}C$ values in step a.) with the actual renewable bio-source carbon content of step b.) for the two resin samples);
 d.) determining the renewable bio-source carbon content of the remaining resin samples in the production run based on said correlation; and
 e.) calculating the renewable bio-content from the renewable bio-source carbon content.

In another embodiment, the present invention is a method to measure the renewable bio-source carbon content of a renewable bioplastic resin produced in a production plant over time (e.g. in a production run), which method includes:
 a.) measuring delta carbon-13 ($\delta^{13}C$) values of at least two renewable bioplastic resin samples throughout a production run;
 b.) determining the actual renewable bio-source carbon content of two renewable bioplastic samples in step a.) with the lowest and the highest $\delta^{13}C$ value;
 c.) correlating the $\delta^{13}C$ values in step a.) with the actual renewable bio-source carbon content of step b.) for the two resin samples); and
 d.) determining indirectly the renewable bio-source carbon content of the remaining resin samples in the production run based on said correlation.

In another embodiment, the present invention is a method to measure the renewable bio-source carbon content of a renewable bioplastic resin produced in a production plant over time (e.g. in a production run), which method includes:
 a.) measuring delta carbon-13 ($\delta^{13}C$) values of at least one renewable bioplastic resin samples throughout a production run;
 b.) determining the actual renewable bio-source carbon content of the renewable bioplastic sample in step a.) or the renewable bioplastic sample in step a.) with the highest $\delta^{13}C$ value;
 c.) correlating the $\delta^{13}C$ values in step a.) with the actual renewable bio-source carbon content of step b.) for the two resin samples); and
 d.) determining the renewable bio-source carbon content of the remaining resin samples in the production run based on said correlation.

In certain embodiments, step a.) of the method comprises measuring delta carbon-13 ($\delta^{13}C$) values of at least two renewable bioplastic resin samples throughout a production run. In certain embodiments, step b.) of the method further comprises determining the actual renewable bio-source carbon content of two renewable bioplastic samples. In one embodiment, step d.) of the method comprises determining indirectly the renewable bio-source carbon content of the remaining resin samples in the production run based on said correlation. In any of the foregoing embodiments, the first step of the method may comprise obtaining at least one or at least two renewable bioplastic resin samples in a production run. In any of the foregoing embodiments, the bioplastic resin samples may be produced in a plant transitioning from non-renewable petroleum-derived starting materials to renewable bio-derived starting materials, for example a plant transitioning from non-renewable petroleum-MEG materials to renewable bio-MEG materials. In certain embodiments, the bioplastic resin sample is PET resin.

The measurement in step d.) can be based on the linear correlation between measured $\delta^{13}C$ values and the actual renewable bio-source carbon content (Carbon-14 or $^{14}C$, measured by AMS, for example). From this linear correlation, the renewable bio-source carbon content of remaining samples in the production can be indirectly determined. One advantage of this method is that, instead of measuring the actual renewable bio-source carbon content ($^{14}C$) of each sample, which can be expensive and time consuming, only a subset of samples (one or two samples) in the production run require $^{14}C$ analysis. Then, the renewable bio-source carbon content of the remaining samples in the production run can be indirectly determined based on the linear correlation.

In some embodiments, the method further comprises calculating the renewable bio-content of the renewable bioplastic resin from the renewable bio-source carbon content. This is done by calculating the relative contribution of the renewable bio-source carbon content relative to the entire renewable bioplastic resin based on a correlation factor.

In a preferred embodiment, the renewable bioplastic resin is renewable bio-polyethylene terephthalate (renewable bio-based PET). In a particular embodiment, the renewable bio-based PET includes renewable bio-monoethylene glycol (MEG) (either fully or partially renewable bio-derived) and non-renewable petroleum-derived terephthalic acid (p-TA).

In a more particular embodiment, the methods described herein are used to measure the renewable bio-source carbon content of a renewable bioplastic resin produced in a production run in a plant transitioning from non-renewable petroleum-derived plastic starting materials to renewable bio-derived bioplastic starting materials. In one embodiment, a method for measuring the renewable bio-source carbon content in a renewable bioplastic resin produced in a production run in a plant transitioning from non-renewable petroleum-derived plastic starting materials to renewable bio-derived bioplastic starting materials comprises:

a.) measuring $\delta^{13}C$ values of the renewable bioplastic resin samples produced in a plant transitioning from non-renewable petroleum-derived starting materials to renewable bio-derived starting materials;

b.) determine the actual renewable bio-source carbon content of two renewable bioplastic samples in step a.) with the lowest and the highest $\delta^{13}C$ value;

c.) correlating the $\delta^{13}C$ values in step a.) with the actual renewable bio-source carbon content of step b.) for the two resin samples);

d.) determining indirectly the renewable bio-source carbon content of the remaining resin samples in the production run based on said correlation; and e.) calculating the renewable bio-content from the renewable bio-source carbon content In a preferred embodiment, the renewable bioplastic resin is renewable bio-based PET. In one embodiment, the non-renewable petroleum-derived plastic starting material is non-renewable petroleum-derived monoethylene glycol (p-MEG) and the renewable bio-derived starting material is renewable bio-derived monoethylene glycol (renewable bio-MEG).

In some embodiments, the method further comprises calculating the renewable bio-content of the renewable bioplastic resin from the renewable bio-source carbon content. This is done by calculating the relative contribution of the renewable bio-source carbon content relative to the entire renewable bioplastic resin based on a correlation factor.

In some embodiments, a method for measuring the renewable bio-carbon content in renewable bio-based PET resins in a production run in a plant transitioning from non-renewable petroleum-MEG materials to renewable bio-MEG comprises:

a.) measuring $\delta^{13}C$ values of the PET resin produced in a plant transitioning from non-renewable petroleum-MEG to renewable bio-MEG;

b.) determine the actual renewable bio-source carbon content of two renewable bioplastic samples in step a.) with the lowest and the highest $\delta^{13}C$ value;

c.) correlating the $\delta^{13}C$ values in step a.) with the actual renewable bio-source carbon content of step b.) for the two resin samples);

d.) determining indirectly the renewable bio-source carbon content of the remaining resin samples in the production run based on said correlation; and e.) calculating the renewable bio-content from the renewable bio-source carbon content In some embodiments, the method further comprises the step of calculating the renewable bio-content of the renewable bio-based PET samples in the production run. This determination is done by calculating the relative contribution of renewable bio-MEG to the entire renewable bio-based PET resin based on a correlation factor.

In a preferred embodiment, the $\delta^{13}C$ values are measured by combustion—Cavity Ring-Down Spectrometry (ORDS). In another preferred embodiment, the $\delta^{13}C$ values are measured by Total Organic Carbon-Cavity Ring-Down Spectrometry (iTOC-CRDS) and the actual renewable bio-source carbon content is determined by Accelerator Mass Spectrometry (AMS).

DETAILED DESCRIPTION

I. Definitions

Figure 1:
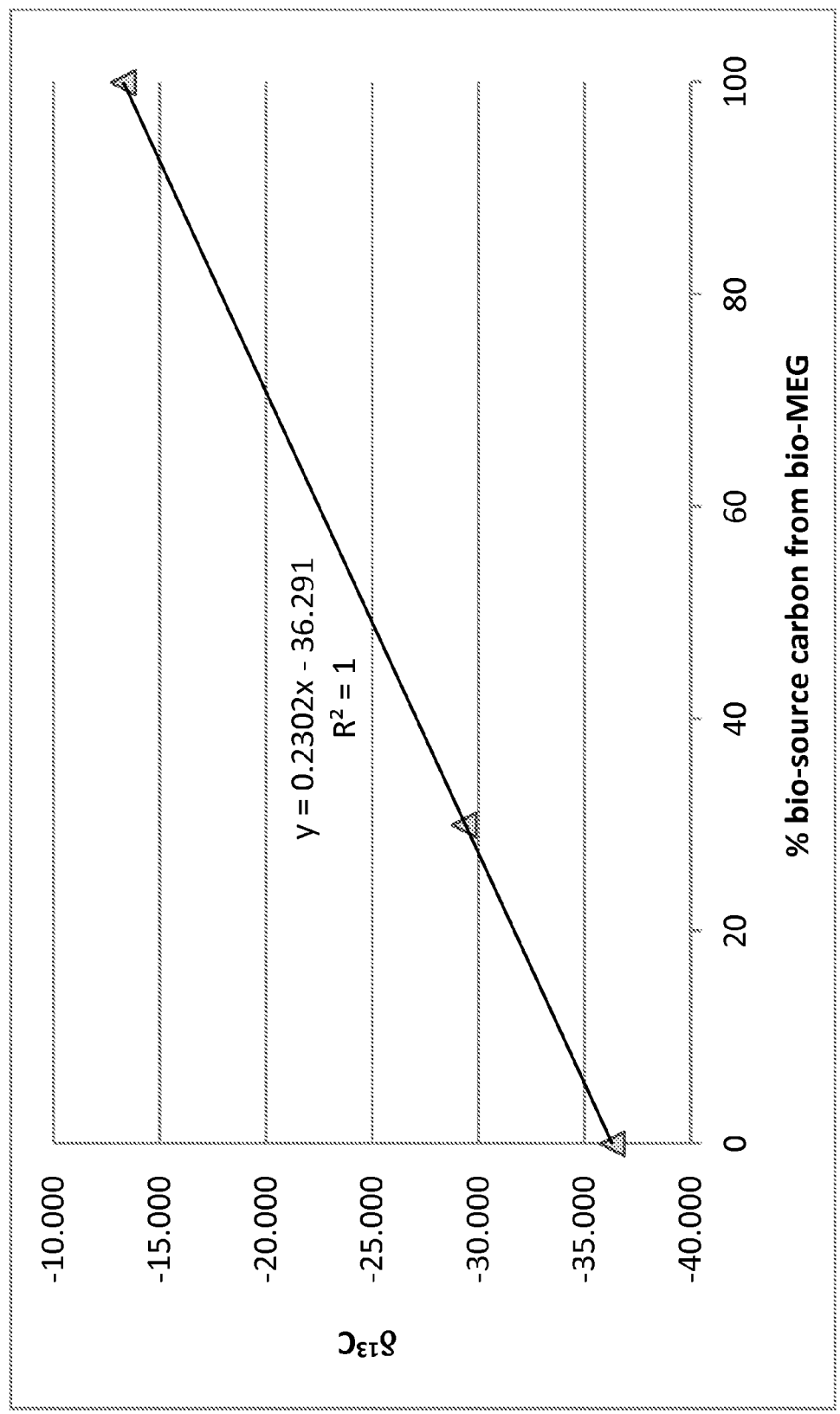
FIG. 1 illustrates a correlation plot of iTOC-CRDS-measured $\delta^{13}C$ values versus actual renewable bio-source carbon content for three MEG samples.

The term "renewable bio-based," as used herein, refers to the inclusion of some component that is derived from at least one renewable biological source.

The term "renewable bio-based PET polymer" used interchangeably with "renewable bio-based PET," as used herein, refers to a polyethylene terephthalate (PET) polymer that comprises at least one component partially or totally derived from at least one renewable bio-based material.

The term "renewable bio-monoethylene glycol" used interchangeably with "renewable bio-MEG," as used herein, refers to monoethylene glycol (MEG) derived from at least one renewable bio-based material.

The term "renewable bio-content," as used herein, refers to the portion of a renewable bioplastic resin that is derived from renewable bio-based materials. The renewable bio-content is generally calculated by multiplying the renewable bio-source carbon content by a conversion factor specific to the molecular composition of a renewable bioplastics repeat unit.

The term "actual renewable bio-source carbon," as used herein, describes the $^{14}C$ content of a sample, as measured by AMS or LSC-spectroscopy, for example.

The term "renewable bio-source carbon," as used herein, describes the carbon content of a sample, as determined by linear correlation of measured $\delta^{13}C$ and measured actual renewable bio-source carbon ($^{14}C$) values.

The term "renewable bio-derived bioplastic starting material," as used herein, refers to materials (e.g. monomers) that are used in the preparation of renewable bioplastics, which materials originate from renewable biological sources. For example, renewable bio-MEG is a renewable bio-derived bioplastic starting material.

The term "renewable bioplastic," as used herein, refers to a plastic that includes at least one component that is partially or totally derived from one renewable bio-based material.

The term "non-renewable petroleum-derived plastic," as used herein, refers to any substance, such as organic, synthetic, and/or processed materials that comprises only non-renewable petroleum-derived components.

The term "non-renewable petroleum-derived plastic starting material," as used herein, refers to starting materials (e.g., monomers) derived from non-renewable petroleum products.

The term "production run," as used herein, refers to a period of time in the manufacturing process during which a renewable bioplastic is produced.

The term "renewable," as used herein, refers to raw materials can be regenerated as same rate as consumption such as crops and plants that can be regrown every year.

The term "non-renewable," as used herein, refers to raw materials that cannot be regenerated at an appreciable rate. For example, fossil oils and non-renewable petroleum take millions of years to form, and therefore are non-renewable.

II. Renewable Bio-Source Carbon

All living matter is composed of three types of carbon: carbon-12 ($^{12}C$), carbon-13 ($^{13}C$) and carbon-14 ($^{14}C$). Carbon-12, which has 6 neutrons and 6 protons, is the most abundant form of carbon on the planet, comprising approximately 98.9% of all carbon isotopes. Carbon-13, which has 7 neutrons and 6 protons, is the second most abundant form of carbon on the plant, comprising approximately 1.1% of all carbon isotopes. Carbon-14, which has 8 neutrons and 6 protons, is the least abundant carbon isotope, and is present in only trace amounts, approximately 14 parts per trillion compared to the total carbon content.

$^{14}C$ is a radioactive isotope, and has a half-life of 5,720 years. The decay product of $^{14}C$ is nitrogen. The formation of $^{14}C$ occurs in the atmosphere, where nitrogen is bombarded with energetic particles originating from the sun such that the nitrogen atom transforms into unstable radioisotope, which rapidly decays to the much more stable $^{14}C$. $^{14}C$ is highly reactive, and rapidly reacts with atmospheric oxygen to give $^{14}CO_2$. The $^{14}CO_2$ then drifts down through the atmosphere to the surface of the Earth, where it is incorporated into living things such as plants, algae, and bacteria, which use the compound for respiration. In this way, $^{14}CO_2$ is propagated through all living things as the plants, algae bacteria are eaten or degraded by other organisms. In fact, $^{14}CO_2$ is uniformly distributed throughout the living ecosystem. In contrast, non-renewable petroleum, although carbon-based, contains no $^{14}C$ because it has been isolated for hundreds of thousands to hundreds of millions of years, during which time any $^{14}C$ that it originally contained has decayed into nitrogen.

Unlike $^{14}C$, which is continuously generated from the interaction of the Sun and the upper atmosphere, the amount of $^{13}C$ is essentially fixed and finite over the period of a several human lifetimes. Most of the $^{13}C$ that is present today has been around since the formation of the solar system. However, due to cycles that introduce more carbon into the atmosphere, bio-renewable bio-derived materials and non-renewable petroleum-derived materials have remarkably different $^{13}C$ levels.

Therefore, by determining the amount of the isotopes of carbon, one can determine the relative renewable bio-source carbon content of a particular material. Renewable bio-based materials will contain $^{12}C$, $^{13}C$ and $^{14}C$. Non-renewable bio-based materials, i.e., non-renewable petroleum-derived materials, will not contain $^{14}C$.

III. Renewable Bioplastic Substrates

The methods of the present invention are directed to measuring the renewable bio-source carbon content of renewable bioplastics, including renewable bioplastic starting materials and the renewable bioplastic resins formed there from.

In one embodiment, the present invention is a method to measure the renewable bio-source carbon content in a renewable bioplastic resin.

In a particular embodiment, the renewable bioplastic is a cellulose plastic, which contains cellulose esters such as cellulose acetate.

In another particular embodiment, the renewable bioplastic is a starch-based renewable bioplastic. Starch-based renewable bioplastics include, but are not limited to, thermoplastics.

In yet another particular embodiment, the renewable bioplastic is a lignin-based renewable bioplastic. Lignin-based renewable bioplastics are derived from wood in the paper milling industry. In another embodiment, the renewable bioplastic is polylactic acid plastic. In another embodiment, the renewable bioplastic is polyhydroxybutyrate plastic. In another embodiment, the renewable bioplastic is a polyurethane. In yet another embodiment, the renewable bioplastic is a polyester. In a preferred embodiment, the renewable bioplastic is poly(ethylene terephthalate) (renewable bio-based PET). In another preferred embodiment, the renewable bioplastic is high density polyethylene (renewable bio-HDPE).

Other suitable renewable bioplastics include, but are not limited to, partially renewable polyesters (polybutylene terephthalate, aliphatic polyesters), renewable bio-polyhydroxyalkonate (renewable bio-PHA), renewable bio-poly-3-hydroxybutrate co-3-hydroxyhexanote (renewable bio-PHBH), renewable bio-poly(hydroxybutyrate-co-valerate) (renewable bio-PHBN), renewable bio-poly-3-hydroxybutyrate (renewable bio-PHB), renewable bio-polybutylene succinate (renewable bio-PBS), renewable bio-poly(butylene succinate-co-adipate) (renewable bio-PBSA), renewable bio-poly(butylene succinate-co-carbonate), renewable bio-polycaprolactone (renewable bio-PCL), renewable bio-cellulose acetate (renewable bio-PH), renewable bio-polylactic acid (renewable bio-PLA) or renewable bio-copoly-L-lactide (renewable bio-CPLA), and naturally occurring polymer, such as starch modified renewable bio-PVA+aliphatic polyester, or corn starch.

The methods described herein are useful to measure the renewable bio-source carbon content of renewable bioplastics derived wholly or in part from renewable bio-mass sources. Renewable bio-sources include, but are not limited to, food and non-food renewable bio-sources such as sugars, starches, corns, natural fibers, sugarcanes, beets, citrus fruits, woody plants, cellulosics, lignocelluosics, hemicelluloses, potatoes, plant oils, other polysaccharides such as pectin, chitin, levan, and pullulan, and a combination thereof. According to a particular embodiment, the methods described herein are used to measure the renewable bio-source carbon content of a renewable bioplastic derived from at least one renewable bio-source material, including, but not limited to, corn, sugarcane, beet, potato, starch, citrus fruit, woody plant, cellulosic lignin, plant oil, natural fiber, oily wood feedstock, and combinations thereof.

In other embodiments, the methods described herein are used to measure the renewable bio-source carbon content of renewable bio-derived starting materials from which renewable bioplastics are ultimately produced. These starting materials may be monomers. For example, PET is manufactured from Fischer esterification of terephthalic acid (TA) and monoethylene glycol (MEG). Renewable bio-based PET (renewable bio-based PET) is produced from Fischer esterification using either renewable bio-derived MEG (renewable bio-MEG), renewable bio-derived TA or both renewable bio-TA and renewable bio-MEG. Methods in the art are known for generating both renewable bio-MEG and renewable bio-TA though chemical and/or renewable biological processes, which ultimately originate with renewable biomass starting materials.

In still other embodiments, the methods described herein are used to measure the renewable bio-source carbon content of a renewable bioplastic resin produced over time in a production facility or plant. In a preferred embodiment, the method is used to measure the renewable bio-source content of renewable bio-based PET resin produced over time in a production facility or plant. In preferred embodiments, a production run is between 1 to 5 hours, between 1 to 10 hours, between 1 to 20 hours, between 1 to 30 hours, between 1 to 40 hours, between 1 to 50 hours, between 1 to 100 hours, between 1 to 150 hours, or between 1 to 200 hours or more. In some embodiments, the production run is continuous and can be between 1 to 2 months, between 1 to 3 months, between 1 to 4 month, between 1 to 5 months, between 1 to 6 months, between 1 to 7 months, between 1 to 8 months, between 1 to 9 months, between 1 to 10 months, between 1 to 11 months, between 1 month to 1 year, between 1 to 2 years or between 1 to 3 years.

In a more particular embodiment, the methods described herein are used to measure the renewable bio-source carbon content of a renewable bioplastic resin produced in a production plant transitioning from non-renewable petroleum-derived plastic starting materials to renewable bio-derived bioplastic starting materials, or in a plant carrying out multiple transitions between non-renewable petroleum-derived plastic starting materials and renewable bio-derived bioplastic starting materials. In a preferred embodiment, the methods described herein are used to measure the renewable bio-source carbon content of a renewable bioplastic resin in a production plant transitioning from non-renewable petroleum-derived plastic starting materials to renewable bio-derived bioplastic starting materials.

A production run is dictated by transitions between non-renewable petroleum-derived and renewable bio-derived starting materials. For example, a production run, in one embodiment, is defined by the time in which a production plant swaps out non-renewable petroleum-derived starting materials (such as p-MEG) with renewable bio-derived starting materials (such as renewable bio-MEG), and then at some point later, switches back to non-renewable petroleum-derived starting materials (such as p-MEG).

The production run, in some embodiments, includes leading and trailing time periods prior to swapping out of starting materials (e.g., "transitioning"). Accordingly, in some embodiments, a production run includes between 1 to 10 hours, between 1 and 15 hours, between 1 and 20 hours, or between 1 and 24 hours before non-renewable petroleum-derived starting materials are swapped out for renewable bio-derived starting materials. In another embodiment, the production run includes between 1 to 5 hours, between 1 to 10 hours, between 1 to 20 hours, between 1 to 30 hours, between 1 to 40 hours, between 1 to 50 hours, between 1 to 100 hours, between 1 to 150 hours, or between 1 to 200 or more hours after the renewable bio-derived starting materials are swapped out for non-renewable petroleum-derived starting materials. In preferred embodiments, a production run is between 1 to 5 hours, between 1 to 10 hours, between 1 to 20 hours, between 1 to 30 hours, between 1 to 40 hours, between 1 to 50 hours, between 1 to 100 hours, between 1 to 150 hours, or between 1 to 200 hours or more. In some embodiments, the production run is continuous and can be between 1 to 2 months, between 1 to 3 months, between 1 to 4 months, between 1 to 5 months, between 1 to 6 months, between 1 to 7 months, between 1 to 8 months, between 1 to 9 months, between 1 to 10 months, between 1 to 11 months, between 1 month to 1 year, between 1 to 2 years or between 1 to 3 years.

In some embodiments, the transitions between non-renewable petroleum-derived plastics to renewable bioplastics are continuous. For example, non-renewable petroleum-derived starting materials are swapped out with renewable bio-derived starting materials, and then non-renewable petroleum-derived starting materials are reintroduced, and the process is repeated without production ceasing. Accordingly, in some embodiments, the production run is continuous through multiple transitions between petroleum-derived starting materials and renewable bio-derived starting materials, and can last between 1 to 2 months, between 1 to 3 months, between 1 to 4 month, between 1 to 5 months, between 1 to 6 months, between 1 to 7 months, between 1 to 8 months, between 1 to 9 months, between 1 to 10 months, between 1 to 11 months, between 1 month to 1 year, between 1 to 2 years or between 1 to 3 years.

In another preferred embodiment, the methods described herein are used to measure the renewable bio-source carbon content of renewable bio-based PET resin produced in a production plant transitioning from p-MEG starting material to renewable bio-MEG starting material. In a more preferred embodiment, the methods described herein are used to measure the renewable bio-source carbon content of renewable bio-based PET resin produced in a production plant transitioning from p-MEG starting material to renewable bio-MEG starting material.

A. Sample Preparation

Because the methods described herein can be used on a multitude of carbon-containing renewable bioplastic resins or renewable bioplastic starting materials, the material analyzed can be of any physical state. Accordingly, in some embodiments, the renewable bioplastic resin or renewable bioplastic starting material is a liquid. In other embodiments, the renewable bioplastic resin or renewable bioplastic starting material is a solid.

In embodiments wherein the renewable bioplastic resin or renewable bioplastic starting material is a liquid, no sample preparation is prior to combustion with CRDS.

In embodiments wherein the renewable bioplastic resin or renewable bioplastic starting material is a solid, the solid must be ground to provide small and uniform pieces. In embodiments wherein the method is used to measure the renewable bio-source carbon content of renewable bio-based PET, it is preferred that the amorphous form of renewable bio-based PET resin is analyzed with the methods described herein.

In certain embodiments, the sample size for iTOC-CRDS $\delta^{13}C$ analysis of liquid renewable bioplastic starting materials, including bio-derived renewable bioplastic starting materials, such as renewable bio-MEG, is between 1 μL and 10 μL, between 2 μL and 9 μL, between 3 μL and 8 μL, between 4 μL and 7 μL, between 5 μL and 6 μL. In a more preferred embodiment, the sample size is between 2 μL and 4 μL. In yet another preferred embodiment, the liquid sample size is about 2 μL.

In other embodiments, the sample size for CRDS $\delta^{13}C$ analysis of solid renewable bioplastic resin, including renewable bio-based PET, is between 1 and 10 mg, between 2 and 9 mg, between 3 and 8 mg, between 4 and 7 mg, between 5 and 6 mg. In a more preferred embodiment, the sample size is approximately 2 mg. The sample can be cryogenically ground and homogenized using liquid nitrogen in a milling device prior to analysis.

Notably, if the methods described herein are used to measure the renewable bio-source carbon content of renewable bioplastic resin produced over a period of time, samples from various time points during the production run should be prepared. The number of samples taken depends on the length of the production run, although a minimum of two samples is required to generate the linear correlation. In more preferred embodiments, 3 samples are taken, 4 samples are taken, 5 samples are taken, 6 samples are taken, 7 samples are taken, 8 samples are taken, 9 samples are taken, 10 samples are taken, 20 samples are taken, 30 samples are taken, 40 samples are taken, 50 samples are taken, 60 samples are taken, 70 samples are taken, 80 samples are taken, 90 samples are taken, or 100 or more samples are taken.

Samples are taken at various intervals depending on the length of the production run. Samples can be taken every 1 minute, every 2 minutes, every 3 minutes, every 4 minutes, every 5 minutes, every 6 minutes, every 7 minutes, every 8 minutes, every 9 minutes, every 10 minutes, every 20 minutes, every 30 minutes, every 40 minutes, every 50 minutes, or every hour. In other embodiments, samples are taken every hour, every 2 hours, every 3 hours, every 4 hours, every 5 hours, every 6 hours, ever 7 hours, every 8 hours, every 9 hours, every 10 hours, every 20 hours, every 24 hours, every 30 hours, every 40 hours, every 48 hours, every 50 hours, every 60 hours, every 70 hours, every 72 hours, every 80 hours, every 90 hours, ever 100 hours or every 200 hours or more. In still other embodiments, samples are taken every day, every 2 days, every 3 days, every 4 days, every 5 days, every 6 days, every week, every 2 weeks, every 3 weeks or every 4 weeks. In yet other embodiments, samples can be taken every 2 months, every 3 months, every 4 months, every 5 months, every 6 months, every 7 months, every 8 months, every 9 months, every 10 months, every 11 months, every 12 months, every 2 years or every 3 years.

If the methods are used to measure the renewable bio-source carbon content of a renewable bioplastic resin in a production plant transitioning from non-renewable petroleum-derived plastic starting materials to bio-derived renewable bioplastic starting materials, samples at time points prior to the transition and after transition can be prepared.

B. Measuring $\delta^{13}C$ Values

After samples of renewable bioplastic reins from various time points in the production run are obtained, the $\delta^{13}C$ values are measured. Resins produced at different time points in the production of the renewable bioplastic resin should be measured individually. Methods of determining the amount of stable (non-radioactive) carbon isotopes, $^{13}C$ and $^{12}C$, in a sample, required to calculate $\delta^{13}C$ values, are known in the art.

In one embodiment, the amount of $^{13}C$ and $^{12}C$ are measured using isotope ratio mass spectrometry (IRMS). Briefly, in IRMS, samples are ionized, and the ionized material is sorted by mass to charge ratio, and then counted. IRMS is currently the method of choice for compound-specific isotope analysis (CSIA). Both liquids and solids can be analyzed depending on how the material is introduced into the instrument. IRMS is similar to AMS in that the sample is ionized and the isotopes are separated and counted. However, since there is a more abundance of $^{13}C$ relative to $^{14}C$, the instrument is significantly lower in cost and easier to run.

In another embodiment, the amount of $^{13}C$ and $^{12}C$ are measured using diffuse reflectance infrared Fourier transform-Nuclear Magnetic Resonance Spectroscopy (DRIFT-NMR). Briefly, in DRIFT-NMR, the interactions of protons of the different carbon isotopes are observed. DRIFT-NMR is currently less favored than IRMS, but allows for the testing of samples that may not be testable by IRMS. The method has an advantage in that it can measure liquid samples directly with little or no sample preparation. However, the instrument has a high cost and carries significant upkeep.

In a preferred embodiment, the amount of $^{13}C$ and $^{12}C$ are measured using cavity ring-down spectroscopy (CRDS). CRDS is the newest method for making CSIA measurements of $^{13}C$ and $^{12}C$, and has become increasing popular due to its relatively low cost, ease of use (not requiring highly trained personnel), compactness, and analysis time. In a more preferred embodiment, CRDS also includes the capability of determining the $^{13}C$ and $^{12}C$ content of carbon in water-based samples. Accordingly, in some embodiments, a total organic carbon analyzer, which measures the $^{13}C$ and $^{12}C$ content of carbon in water-based samples, is interfaced to a CRDS instrument (iTOC-CRDS).

Briefly, CRDS is a sensitive absorption measurement technique for trace gas detection. The sample is combusted to $^{14}CO_2$, $^{13}CO_2$, $^{12}CO_2$ and water. In one embodiment, the combustion is carried out at temperatures between 900° C. and 2000° C., more preferably between 1600° C. and 1800° C. Once combusted, the carbon dioxide gases are carried into an optical cavity equipped with two or more high reflectivity dielectric mirrors for measurement. A laser, exclusive to $^{12}CO_2$ or $^{13}CO_2$, is introduced into the cavity through one of the mirrors. At some time t=0, the laser is switched off. The light remaining in the cavity then decays with time due to a combination of mirror losses and absorption losses. A detector measuring the intensity of light transmitted by the cavity is then used to measure the rate of its decay. A measurement consists of observing the rate of decay of light in the optical cavity, and then relating this rate of decay to the concentration of absorbing species. The concentration of the absorbing species, $^{13}CO_2$ or $^{12}CO_2$, can then be determined.

After the concentrations of $^{13}C$ and $^{12}C$ are measured, the ratio of the two isotopes, $\delta^{13}C$, is determined. In a preferred embodiment, $\delta^{13}C$ is calculated by taking into account the Vienna Pee Dee Belemnite (VPDB) standard from the National Institute of Standards and Technology (NIST). The $\delta^{13}C$, usually expressed in parts per thousand (or per mil, ‰), of a given sample can be determined using the formula below:

$$\delta^{13}C = \left( \frac{^{13}C/^{12}C_{sample}}{^{13}C/^{12}C_{VPDE}} - 1 \right) \times 1000$$

Differences exist in the $\delta^{13}C$ values for different types and species of plants, for the same plants grown in different geographic regions, and even for the same plants grown in the same geographic regions due to seasonal variations and changes in fertilizers. Notably, the $\delta^{13}C$ should only be measured if the renewable bioplastic resin or renewable bioplastic starting material is from the same feedstock geographically. Accordingly, in a preferred embodiment, the renewable bio-derived feedstock for the renewable bioplastic is from a single source. Accordingly, in a preferred embodiment, the non-renewable petroleum-derived feedstock for the renewable bioplastic is from a single source. A new correlation plot should be acquired for each renewable bioplastic resin production run to avoid these differences.

C. Correlating $\delta^{13}C$ to the Actual Renewable Bió-Source Carbon Content

In order to correlate the $\delta^{13}C$ values to the $^{14}C$ content (actual renewable bio-source carbon), the actual renewable bio-source carbon content of the renewable bioplastic or renewable bioplastic starting material must be measured.

Methods of determining actual renewable bio-source carbon content are well-known in the art. In a preferred embodiment, the actual renewable bio-source carbon content is measured on a portion of the same material used to measure the $\delta^{13}C$ value.

In one embodiment, the actual renewable bio-source carbon content is measured by liquid scintillation counting (LSC). Briefly, in LSC, a carbon-containing sample is oxidized to carbon dioxide, and then converted through a number of synthetic processes to benzene. A scintillation agent is then mixed with the benzene, upon which the scintillation agent will emit a photon hit by the electron emitted by the $^{14}C$. LSC instruments then count the number of photons emitted over a defined period to calculate the amount of actual renewable bio-source carbon content in a given sample.

In another embodiment, the actual renewable bio-source carbon content is measured by Accelerator Mass Spectrometry (AMS). Briefly, in AMS, a sample is oxidized to carbon dioxide, and is subsequently reduced to elemental carbon (graphite form). The sample is then hit with a high energy electron beam that ionizes the carbon. The ionized sample is analyzed by mass spectrometry to determine actual renewable bio-source carbon content.

The actual renewable bio-source carbon content is reported using LSC or AMS as a percentage of the total renewable bio-based carbon. For example, in a sample containing only non-renewable petroleum-derived carbon, the renewable bio-source carbon content would be 0%. For a sample containing only renewable bio-derived carbon, the renewable bio-source carbon content would be 100%. For a sample containing a mixture of non-renewable petroleum-derived and renewable bio-derived carbon, the renewable bio-source carbon content will be between 0% and 100%.

In preferred embodiments, the actual renewable bio-source carbon content of the renewable bioplastic resin or renewable bioplastic starting material from various points in the production thereof are measured. In a more preferred embodiment, the actual renewable bio-source carbon content of at least two samples in a given production run of the renewable bioplastic or renewable bioplastic starting material is measured, corresponding to the samples with the highest and lowest $\delta^{13}C$ values. In yet another preferred embodiment, the actual renewable bio-source carbon content of at least one sample in the production of the renewable bioplastic or renewable bioplastic starting material is measured, corresponding to the sample with the highest $\delta^{13}C$ value. The actual renewable bio-source carbon content samples are used to "anchor," or standardize, the $\delta^{13}C$ values of the production run. Generally, 0% renewable bio-source carbon content correlates with a lower (more negative) $\delta^{13}C$, whereas 100% renewable bio-source carbon content correlates with a higher (less negative) $\delta^{13}C$.

Once the actual renewable bio-source carbon content for at least one sample in a production run is determined, a linear correlation is made using one or more actual renewable bio-source carbon content measurements and the corresponding $\delta^{13}C$ values for the same production run.

A plot of $\delta^{13}C$ values versus actual renewable bio-source carbon content is established. A linear regression determines the slope and intercept of the correlation plot that defines the line:

$$y=mx+b;$$

where y is the $\delta^{13}C$, m is the slope, x is the renewable bio-source carbon content, and b is the intercept.

In preferred embodiments, the linear correlation of $\delta^{13}C$ values to actual renewable bio-source carbon is used to determine the renewable bio-source carbon content in the remaining samples in the production run (i.e. samples in which only $\delta^{13}C$ values were determined, not samples where both $\delta^{13}C$ values and actual renewable bio-source carbon content were determined). Measuring the percentage of renewable bio-source carbon for the remaining samples in the production run is based on the linear correlation of $\delta^{13}C$ measurements with actual renewable bio-source carbon content. In preferred embodiments, the method can measure the renewable bio-source carbon content in samples differing by as little as 2% (or ±1%).

In one embodiment, the average standard deviation between a given $\delta^{13}C$ value and the renewable bio-source carbon content of a sample is between 0.05 to 0.25. In a preferred embodiment, the average standard deviation is less than about 0.125, more preferably less than about 0.100.

D. Measuring the Renewable Bio-Content in a Renewable Bioplastic

In preferred embodiments, the method is used to measure the renewable bio-content content of a renewable bioplastics. Typically, this measurement is performed when only one component (i.e. monomer) of the renewable bioplastic is from a renewable bio-source. Accordingly, to measure the renewable bio-content of a renewable bioplastic, a conversion factor based on (1) the relative weight ratio of the renewable bio-derived component/monomer relative to the entire polymeric unit and (2) the relative contribution of carbons in the polymeric unit that originate from the renewable bio-derived component/monomer. In particular, a conversion factor according to the following formula is determined:

$$\text{Conversion factor } (1.5625) = \frac{a}{b}$$

where, a=weight percentage (31.25 wt %) of the renewable bio-derived component in the renewable bioplastic $$\frac{60 \frac{g}{mol} (MEG \text{ in a } PET \text{ repeat unit})}{192 \frac{g}{mol} (PET \text{ repeat unit})} \times 100 =$$

31.25 wt % of MEG in a PET repeat unit b=percentage of carbon (20%) derived from MEG in the renewable bioplastic $$\frac{2 \text{ carbons } (MEG \text{ in a } PET \text{ repeat unit})}{10 \text{ carbons } (PET \text{ repeat unit})} \times 100 =$$

20% carbon from MEG in a PET repeat unit

For example, the weight percentage of renewable bio-MEG in renewable bio-based PET, formed from renewable bio-MEG and p-TA is 31.25 wt %. The repeat unit of PET has 10 carbons, two of which are derived from MEG, and eight from TA. Therefore, a renewable bio-based PET repeat unit made from renewable bio-MEG and p-TA will have, at most, 20% renewable bio-derived carbons (corresponding to 2/10). According, the conversion factor for renewable bio-based PET is 1.5625 (corresponding to 31.25 wt %/20%).

To measure the renewable bio-content of a particular component of a resin—such as the renewable bio-content of bio-based PET formed from renewable bio-MEG, the renewable bio-source carbon content determined by the correlation plot is multiplied by the conversion factor.

EXAMPLES

Example 1—Measurement of Renewable Bio-Source Carbon Using iTOC-CRDS

Chemicals, Reagents, and Devices
  Methanol.
  Dewar filled with liquid nitrogen.
  Retsch CryoMill equipped with 50 mL stainless steel (SS) jar and 25 mm SS grinding ball.
  Ohaus Explorer E1D120 Analytical Balance (Max 4100 g).
  Mettler Toledo XP6 Microbalance (Max 6.1 g) equipped with cleaning brush.
  OI Analytical Aurora Model 1030.
  OI Analytical Solids Model 1030 equipped with large quartz cups (open bottom).
  Picarro Cavity Ring Down Spectrometer—Isotopic $CO_2$ G1111-i.
  Ultra High Purity Oxygen—outlet pressure 60 psi.
  Compressed air.
  Glass wool.
  SS tweezers.
  SS spatula.
  SS tray for holding large quartz cups.
  Small brush.
  Funnel.
  Hamilton gas tight syringe—10 µL.
  Trace Clean Clear Borosilicate Glass Vials—20 mL with PTFE-faced Septa in Open Top Cap Precleaned (VWR Cat No.: 89093-854).
  GC auto-sampler vial caps—National Scientific DP (dual purpose) blue polypropylene with ivory PTFE/red rubber septa (National No.: C4000-51B, VWR Cat. No.: 66030-008).

Cautions
  Cross contaminations of other substances can occur. Use caution when handling sample cups.

Standard Preparation
  Monoethylene Glycol (100% Petro-Based and 100% Renewable Bio-Source):
  Approximately 2 mL of each standard/sample was certified by an external laboratory, such as Beta Analytic (Miami, Fla.) or University of Georgia/Center for Applied Isotope Studies (UGA/CAIS), for actual renewable bio-source content determination of radiocarbon ($^{14}C$) by ASTM method 6866-08a using Accelerator Mass Spectrometry (AMS).

PET Resin (100% Petro-Based and Highest Renewable Bio-Source Produced from Renewable Bio-MEG):
  Using the large capacity analytical balance, the weight of the 50 mL SS jar with grinding ball was tared. Approximately 5 g of resin was weighed in the jar. The jar was milled in a CryoMill with the following milling parameters:

| | |
|---|---|
| Pre-Cooling Frequency | 5.0 Hz |
| Pre-Cooling Cryo Cycles | 1 |
| Pre-Cooling Time | 5.0 min |
| Grinding Frequency | 25.0 Hz |
| Grinding Cryo Cycles | 1 |
| Grinding Time | 2.5 min |

The ground resin was collected into a 20-mL glass vial using a funnel and brush. A few grams of each ground resin was sent to an external laboratory for renewable bio-source content determination of radiocarbon ($^{14}C$) by ASTM method 6866-08a using Accelerator Mass Spectrometry (AMS).

The sample with the highest renewable bio-source content was measured initially using the iTOC-CRDS. The samples and standards were from the same sources to ensure reliable results.

MEG Sample Preparation
  A 10-µL syringe was cleaned with methanol. The syringe was dried using compressed air. Using the syringe, 2 µL of the MEG was dispensed into a preconditioned quartz cup. Using tweezers, the cup was placed into the riser of the Solids module and the analysis was started. Each MEG sample submitted to the external laboratory was analyzed in triplicate. Two samples were used to correlate relative $\delta^{13}C$ values to absolute renewable bio-source carbon values.

Note: Data from the first run of the day should always be omitted. Allow enough time for the riser to cool before placing another cup with MEG into the riser. Enough time has elapsed after the vacuum pump has stopped cycling.

PET Resin Preparation

SS tweezers were used to place the cup on the microbalance and tare the weight. A SS spatula was used to place approximately 2 mg (±0.1 mg) of the ground PET resin into a preconditioned quartz cup. Using tweezers, the cup was placed into the riser of the Solids module and the analysis was started. The 100% petro-based sample and subsequent samples were analyzed in triplicate until the highest renewable bio-source content sample is identified. Two samples (100% petro-based and highest renewable bio-source produced) were submitted to an external laboratory for renewable bio-source carbon content determination. These two samples will be used to correlate relative $\delta^{13}C$ values to absolute renewable bio-source carbon values.

| iTOC-CRDS Instrument Parameters | |
| --- | --- |
| Method | bPET 900 C. 2 min |
| Mode | Solids TC w/CRDS |
| Sample Volume | 8.0 mL |
| System Pressure | 20 psi |
| Drain Time | 15 sec |

React/Detect Times (min:sec) and Temperatures

| | React | Detect |
| --- | --- | --- |
| TIC | 1:30, 70° C. | 3:00, 70° C. |
| TOC/TC | 2:00, 98° C. | 3:00, 98° C. |
| POC | 60° C. | 2:00, 400° C. |
| Solids | 3:00, 900° C. | 3:00 |

| Configuration-Sample Introduction-Solids | |
| --- | --- |
| Standby Temp. | 900° C. |
| Thermocouple Offset | 100° C. |
| Cup Conditioning Time | 1:30 |
| Sample Prime Volume | 5 mL |
| Replicate Prime Volume | 1 mL |
| Sample Chase Volume | 0 mL |
| Fill time | 0:10 |
| Purge Time | 0:20 |
| Purge Cycles | 3 |

| Configuration-Sample Introduction-Solids/CRDS | |
| --- | --- |
| Initial Sample Split Fraction | 20% |
| Solids EFC Standby Flowrate | 30 mL/min |
| Target C12 Concentration | 4000 ppmv |
| CRDS Sniff Detect Time | 2:00 |
| CRDS Baseline Return Delay Time | 2:30 |
| CRDS Pulse Detect Time | 7:00 |

Use First Sniff for all CRDS Samples

| Configuration-Advanced-Syringe Pump | |
| --- | --- |
| Sample Aspirate Speed | 20% |
| Sample Dispense Speed | 70% |

Preparation of iTOC-CRDS

Placed system in Standby mode.

Performed weekly CRDS detector internal calibrations by allowing the CRDS to sniff atmospheric $CO_2$ for 30 min.

Conditioned cups at 900° C. using Solids module.

Analyzed a control PET resin sample daily to adjust necessary $\delta^{13}C$ offset due to CRDS detector drift.

Example 2—Linearity, Accuracy and Precision on MEG from Renewable Bio-Source in MEG FIG. 1 shows a correlation plot of iTOC-CRDS measured $\delta^{13}C$ values versus actual renewable bio-source contents (mixed with known ratios containing MEG from non-renewable petroleum and renewable bio-source) for three MEG samples. Table 1, below, shows a comparison of the actual renewable bio-source content and the measured renewable bio-source content calculated from the trend line in FIG. 1. A linear regression was applied to determine the slope and intercept of the correlation plot. This information was used to calculate the renewable bio-source content in samples.

TABLE 1

Comparison of the actual renewable bio-source content and the measured renewable bio-source content calculated from the trend line in FIG. 1.

| MEG | % Renewable bio-source carbon (Actual) | $\delta^{13}C$ (iTOC-CRDS) | % Renewable bio-source carbon (iTOC-CRDS-calculated from linear correlation plot) |
| --- | --- | --- | --- |
| Petro-based | 0.0 | −36.320 | −0.1 |
| Renewable bio-based | 100.0 | −13.280 | 100.0 |
| Laboratory prepared mixture | 30.1 | −29.330 | 30.2 |

Figure 2:
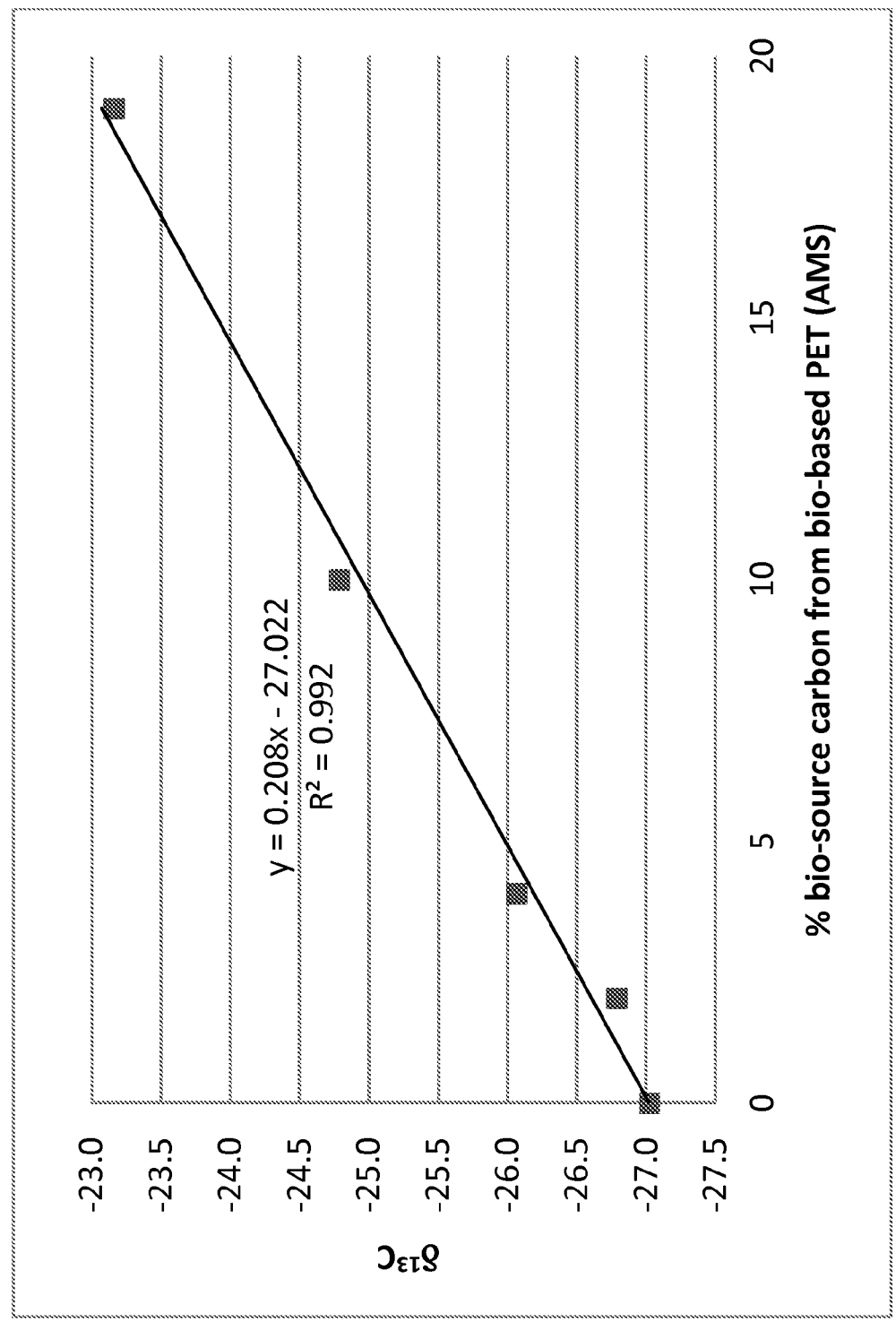
FIG. 2 illustrates a correlation plot of iTOC-CRDS-measured $\delta^{13}C$ values versus AMS-measured renewable bio-source carbon content for five PET films.

Example 3—Linearity, Accuracy and Precision on MEG from Renewable Bio-Source in PET Resin FIG. 2 shows a correlation plot of iTOC-CRDS measured $\delta^{13}C$ values versus AMS-measured renewable bio-source carbon content for five PET films. A linear regression was applied to determine the slope and intercept of the correlation plot. This information was used to calculate the renewable bio-source content in the PET film samples. Table 2 shows a comparison of the actual, AMS-measured, and iTOC-CRDS-calculated (from linear correlation plot in FIG. 2) renewable bio-source content in PET films.

TABLE 2

Comparison of the actual, AMS-measured, and iTOC-CRDS-calculated (from linear correlation plot in FIG. 2) renewable bio-source content in PET films.

| PET Films | iTOC-CRDS $\delta^{13}C$ | Actual % Renewable bio-source carbon | AMS % Renewable bio-source carbon | iTOC-CRDS-calculated from linear correlation plot % Renewable bio-source carbon |
| --- | --- | --- | --- | --- |
| Petro-based | −27.027 | 0 | 0 | 0 |
| Renewable bio-based | −23.162 | 20 | 19 | 19 |

TABLE 2-continued

Comparison of the actual, AMS-measured, and iTOC-CRDS-calculated (from linear correlation plot in FIG. 2) renewable bio-source content in PET films.

| PET Films | iTOC-CRDS $\delta^{13}C$ | Actual | AMS | iTOC-CRDS-calculated from linear correlation plot |
|---|---|---|---|---|
| | | % Renewable bio-source carbon | | |
| Laboratory prepared mixtures | −24.787 | 11 | 10 | 11 |
| | −26.067 | 4 | 4 | 5 |
| | −26.792 | 2 | 2 | 1 |

Table 3 shows replicate iTOC-CRDS $\delta^{13}C$ measurements for 12 PET resin samples. The average standard deviation (Avg. Std. Dev.) and percent relative standard deviation (% RSD) was 0.126‰ and 0.49%, respectively. Based on 3× average standard deviation, samples with renewable bio-carbon content differing by 2% or ±1% can be reliably differentiated by the method.

0.126‰ (average $\delta^{13}C$ std. deviation)×3=0.378‰ $\delta^{13}C$ 0.378‰/0.180 (slope from correlation plot, FIG. 3)=2.1% or ±1.05% Renewable bio-source Carbon in PET Resin

TABLE 3

Replicate iTOC-CRDS $\delta^{13}C$ measurements for 12 PET resin samples.

| Sample # | % carbon from bio-source in PET resin (AMS) | iTOC-CRDS $\delta^{13}C$ | iTOC-CRDS $\delta^{13}C$ (Average) | iTOC-CRDS $\delta^{13}C$ (Std. Deviation) | iTOC-CRDS $\delta^{13}C$ (% RSD) |
|---|---|---|---|---|---|
| 1 | 0 | −27.866 | −28.017 | 0.148 | 0.53 |
| | | −28.161 | | | |
| | | −28.024 | | | |
| 2 | 1 | −27.865 | −27.929 | 0.064 | 0.23 |
| | | −27.930 | | | |
| | | −27.993 | | | |
| 3 | 5 | −27.133 | −27.091 | 0.064 | 0.24 |
| | | −27.017 | | | |
| | | −27.122 | | | |
| 4 | 10 | −26.146 | −26.130 | 0.080 | 0.31 |
| | | −26.043 | | | |
| | | −26.201 | | | |
| 5 | 12 | −25.842 | −25.944 | 0.094 | 0.36 |
| | | −26.027 | | | |
| | | −25.963 | | | |
| 6 | 15 | −25.019 | −25.066 | 0.125 | 0.50 |
| | | −24.971 | | | |
| | | −25.208 | | | |
| 7 | 17 | −24.860 | −25.123 | 0.251 | 1.00 |
| | | −25.150 | | | |
| | | −25.359 | | | |
| 8 | 18 | −24.573 | −24.662 | 0.080 | 0.32 |
| | | −24.727 | | | |
| | | −24.687 | | | |
| 9 | 19 | −24.406 | −24.622 | 0.219 | 0.89 |
| | | −24.615 | | | |
| | | −24.844 | | | |
| 10 | 20 | −24.493 | −24.374 | 0.105 | 0.43 |
| | | −24.336 | | | |
| | | −24.294 | | | |
| 11 | 18 | −24.707 | −24.914 | 0.187 | 0.75 |
| | | −25.070 | | | |
| | | −24.965 | | | |
| 12 | 15 | −25.574 | −25.563 | 0.094 | 0.37 |
| | | −25.652 | | | |
| | | −25.464 | | | |
| | | | Avg Std. Dev. 0.126 | | Avg. % RSD 0.49 |

Figure 3:
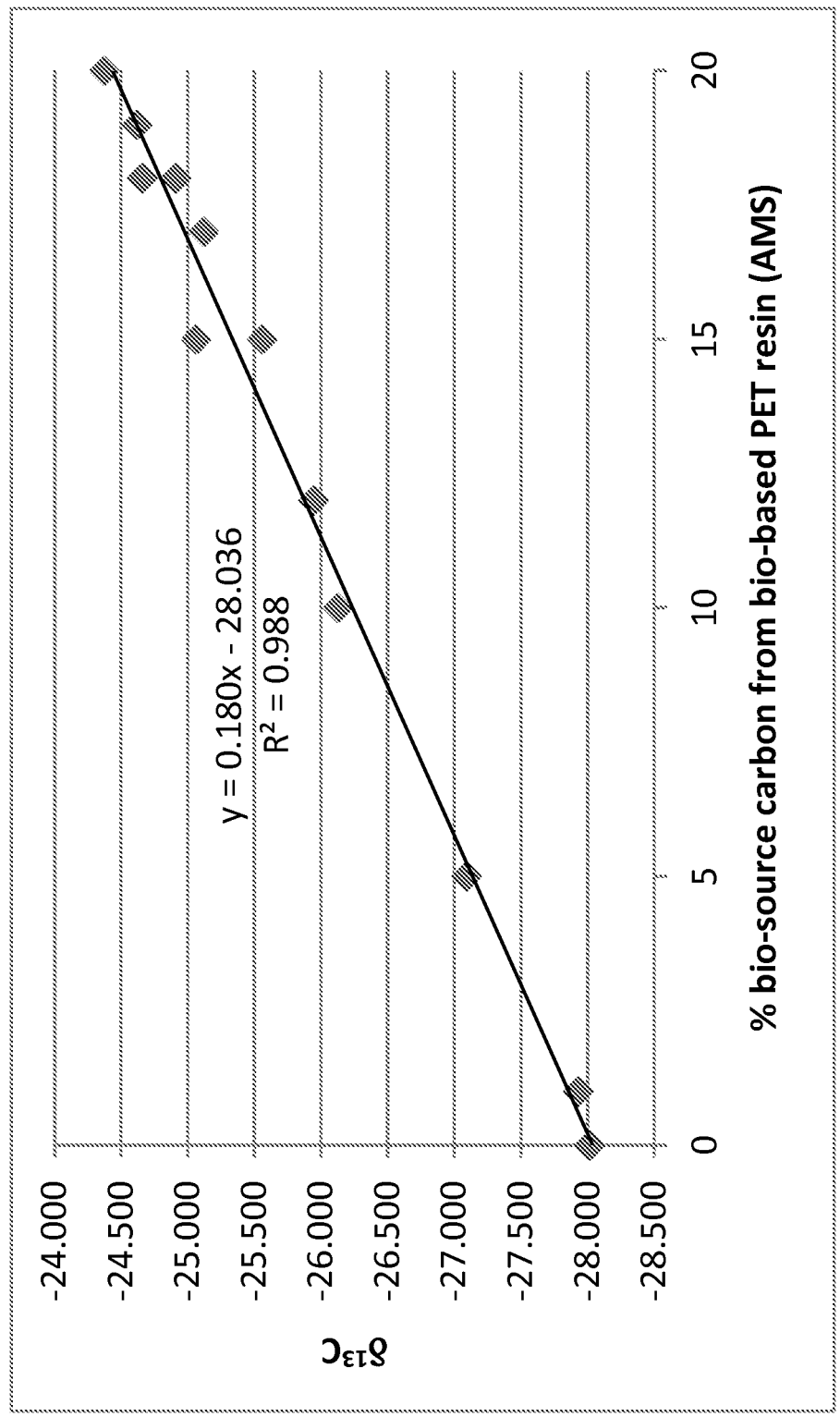
FIG. 3 illustrates a correlation plot of iTOC-CRDS-measured $\delta^{13}C$ values versus AMS-measured renewable bio-source carbon values for a PET resin production run.

Table 4 shows a comparison of AMS-measured renewable bio-source content in PET resin versus renewable bio-source content in PET resin calculated from the linear trend line in FIG. 3.

TABLE 4

Comparison of AMS-measured renewable bio-source content in PET resin versus renewable bio-source content in PET resin calculated from the linear trend line in FIG. 3.

% Renewable bio-source carbon in PET resin

| AMS | iTOC-CRDS-calculated from linear correlation | Absolute Difference |
|---|---|---|
| 0 | 0 | 0 |
| 1 | 1 | 0 |
| 5 | 5 | 0 |
| 10 | 11 | 1 |
| 12 | 12 | 0 |
| 15 | 17 | 2 |
| 17 | 16 | 1 |
| 18 | 19 | 1 |
| 19 | 19 | 0 |
| 20 | 20 | 0 |
| 18 | 17 | 1 |
| 15 | 14 | 1 |

Figure 4:
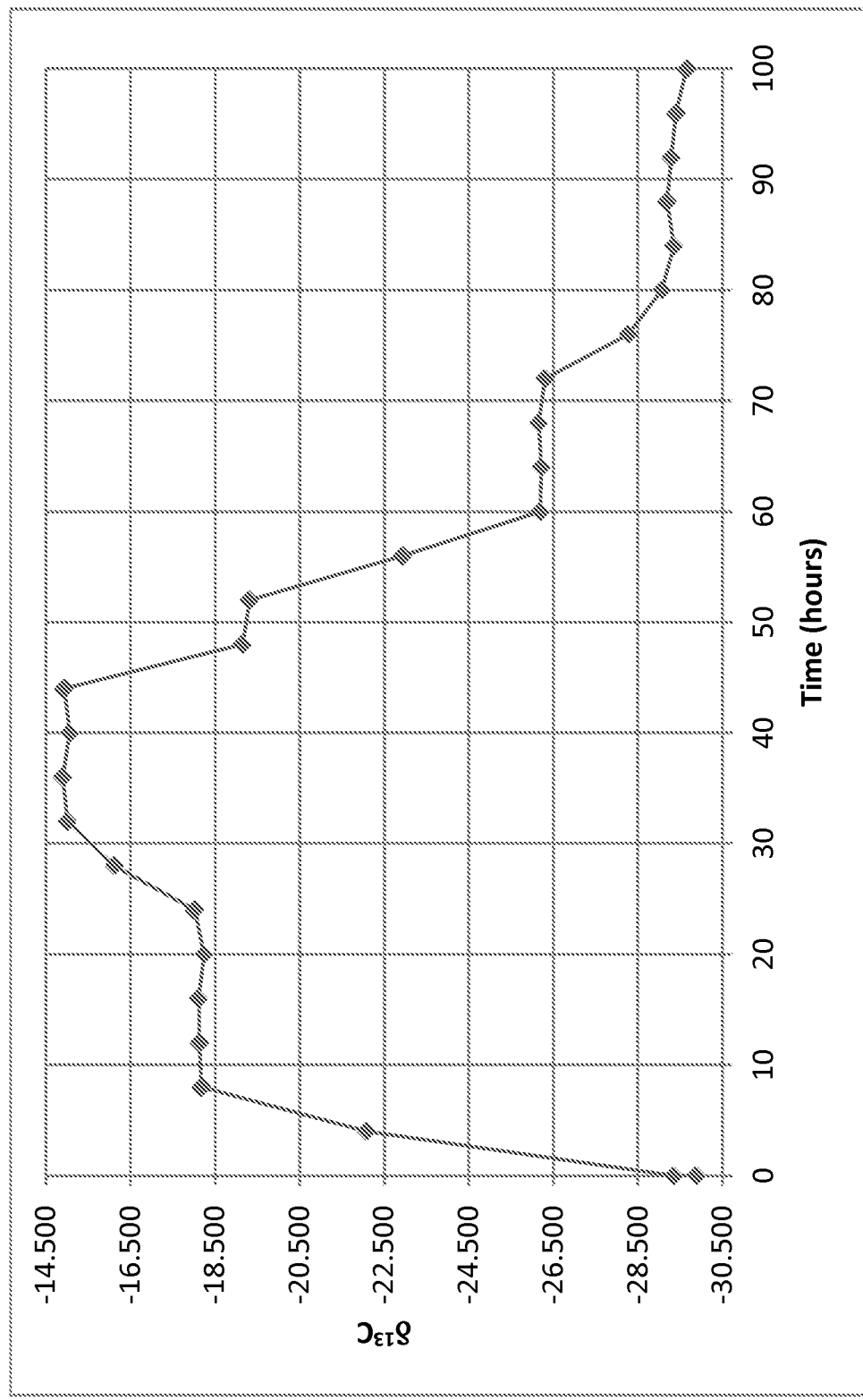
FIG. 4 illustrates iTOC-CRDS-measured $\delta^{13}C$ values for a number of MEG samples collected over a period of 100 hours during which production was converted from petro-PET resins to renewable bio-based PET resins and back to petro-PET resins by replacing petro-MEG with renewable bio-MEG and then switching back to petro-MEG.
Figure 5:
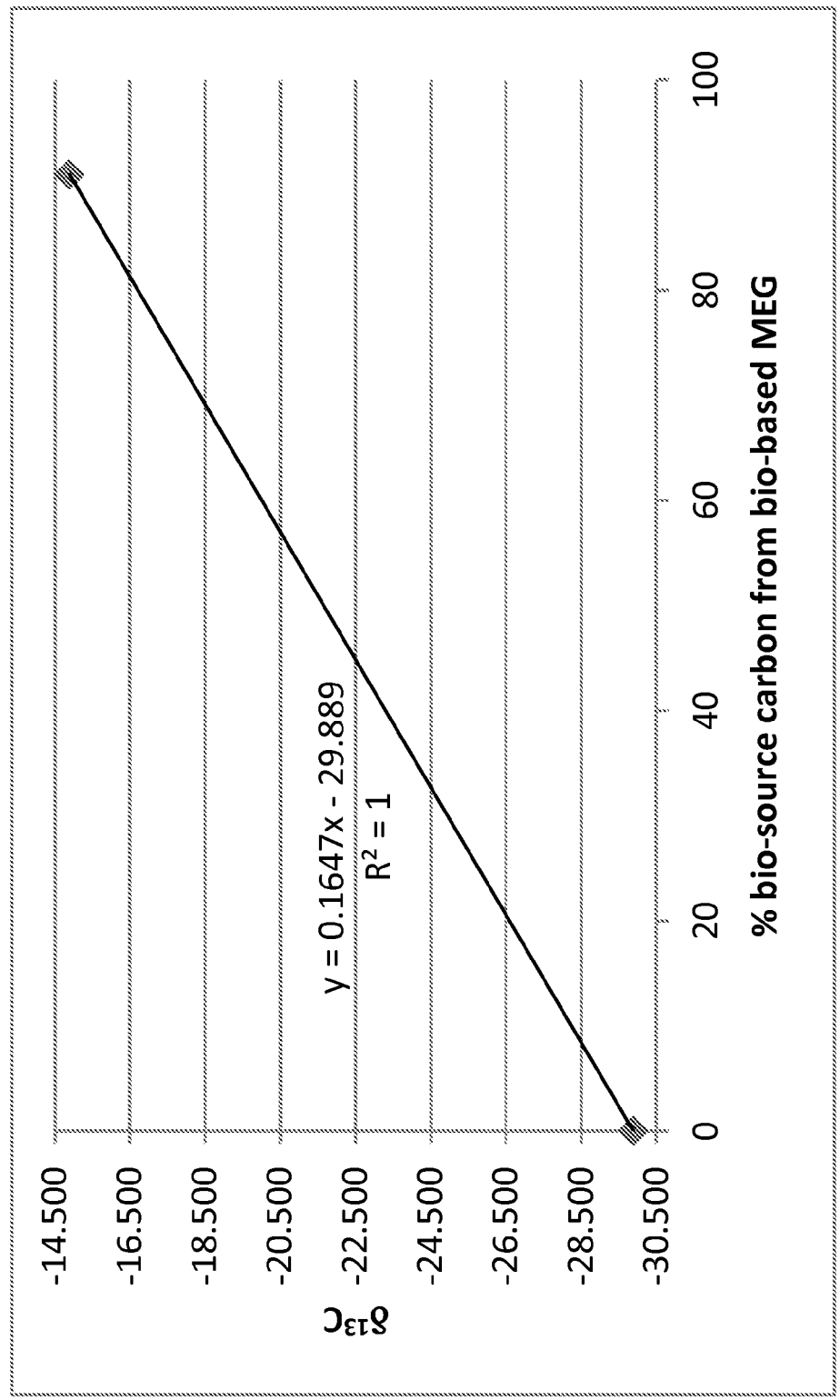
FIG. 5 illustrates a linear correlation plot established using iTOC-CRDS-measured $\delta^{13}C$ values versus AMS-measured renewable bio-source carbon values for the MEG conversion production run in Table 5 in Example 4.
Figure 6:
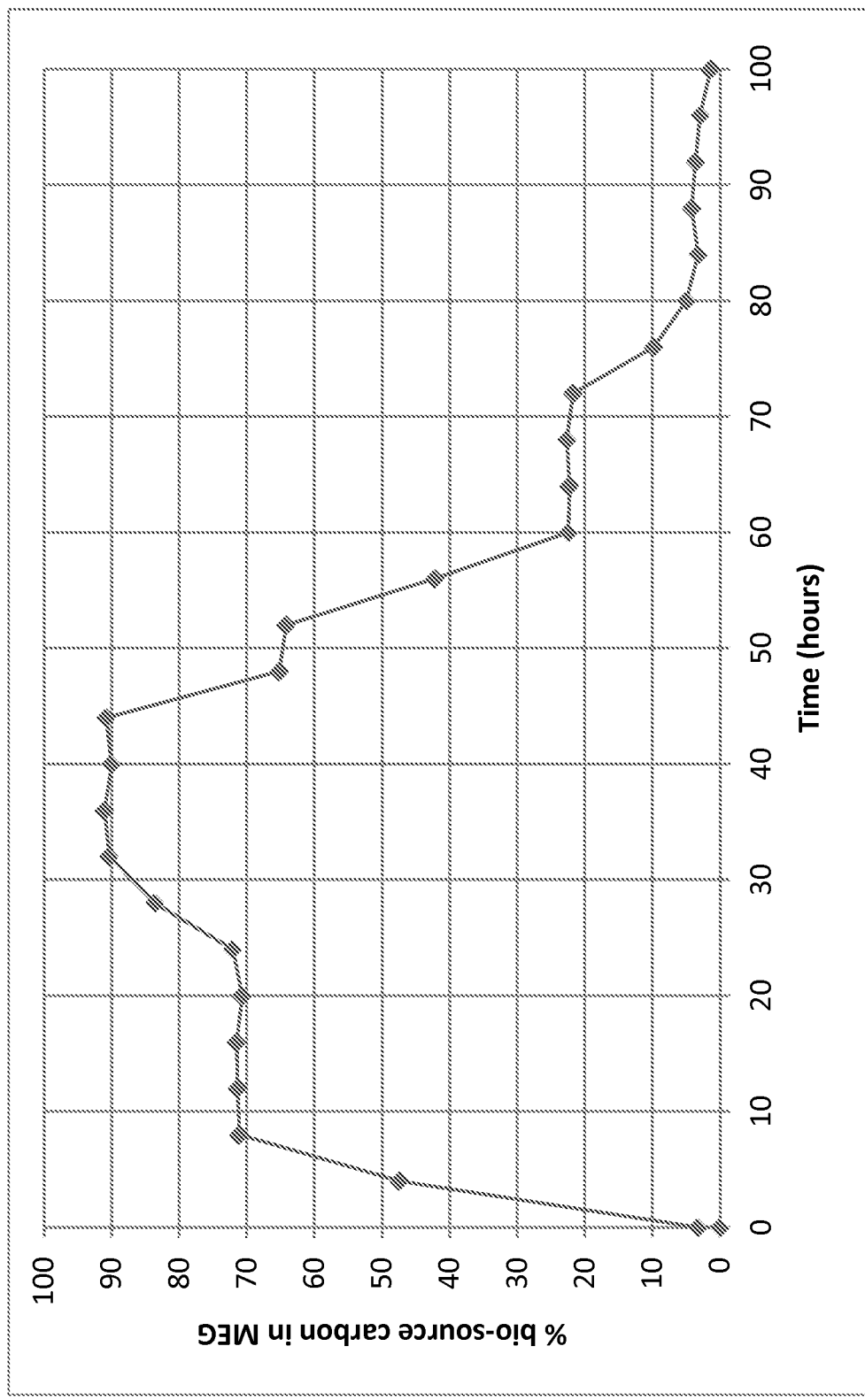
FIG. 6 illustrates the renewable bio-source carbon content of MEG calculated from the correlation plot in FIG. 5.

Example 4—Measurement of $\delta^{13}C$ Values and Calculated Renewable Bio-Source Carbon in MEG from Renewable Bio-Source in MEG Using iTOC-CRDS Table 5 shows the iTOC-CRDS measured $\delta^{13}C$ values and the calculated renewable bio-source carbon values for MEG samples over time for the production run in FIG. 4. Percent renewable bio-source carbon values are calculated using the linear trend line equation in FIG. 5.

TABLE 5 iTOC-CRDS measured $\delta^{13}C$ values and calculated renewable bio-source carbon values for MEG samples over time for the production run in FIG. 4.

| Time (hours) | $\delta^{13}C$ in MEG (Average) | % carbon from renewable bio-source in MEG (Correlation Plot) |
|---|---|---|
| 0 | −29.889 | 0 |
| 0 | −29.352 | 3 |
| 4 | −22.085 | 47 |
| 8 | −18.182 | 71 |
| 12 | −18.137 | 71 |
| 16 | −18.113 | 72 |
| 20 | −18.245 | 71 |
| 24 | −18.021 | 72 |
| 28 | −16.121 | 84 |
| 32 | −15.012 | 90 |
| 36 | −14.898 | 91 |
| 40 | −15.068 | 90 |
| 44 | −14.937 | 91 |
| 48 | −19.152 | 65 |
| 52 | −19.323 | 64 |
| 56 | −22.946 | 42 |
| 60 | −26.195 | 22 |
| 64 | −26.219 | 22 |
| 68 | −26.159 | 23 |
| 72 | −26.309 | 22 |
| 76 | −28.276 | 10 |
| 80 | −29.070 | 5 |
| 84 | −29.355 | 3 |
| 88 | −29.196 | 4 |
| 92 | −29.293 | 4 |
| 96 | −29.405 | 3 |
| 100 | −29.658 | 1 |

Figure 7:
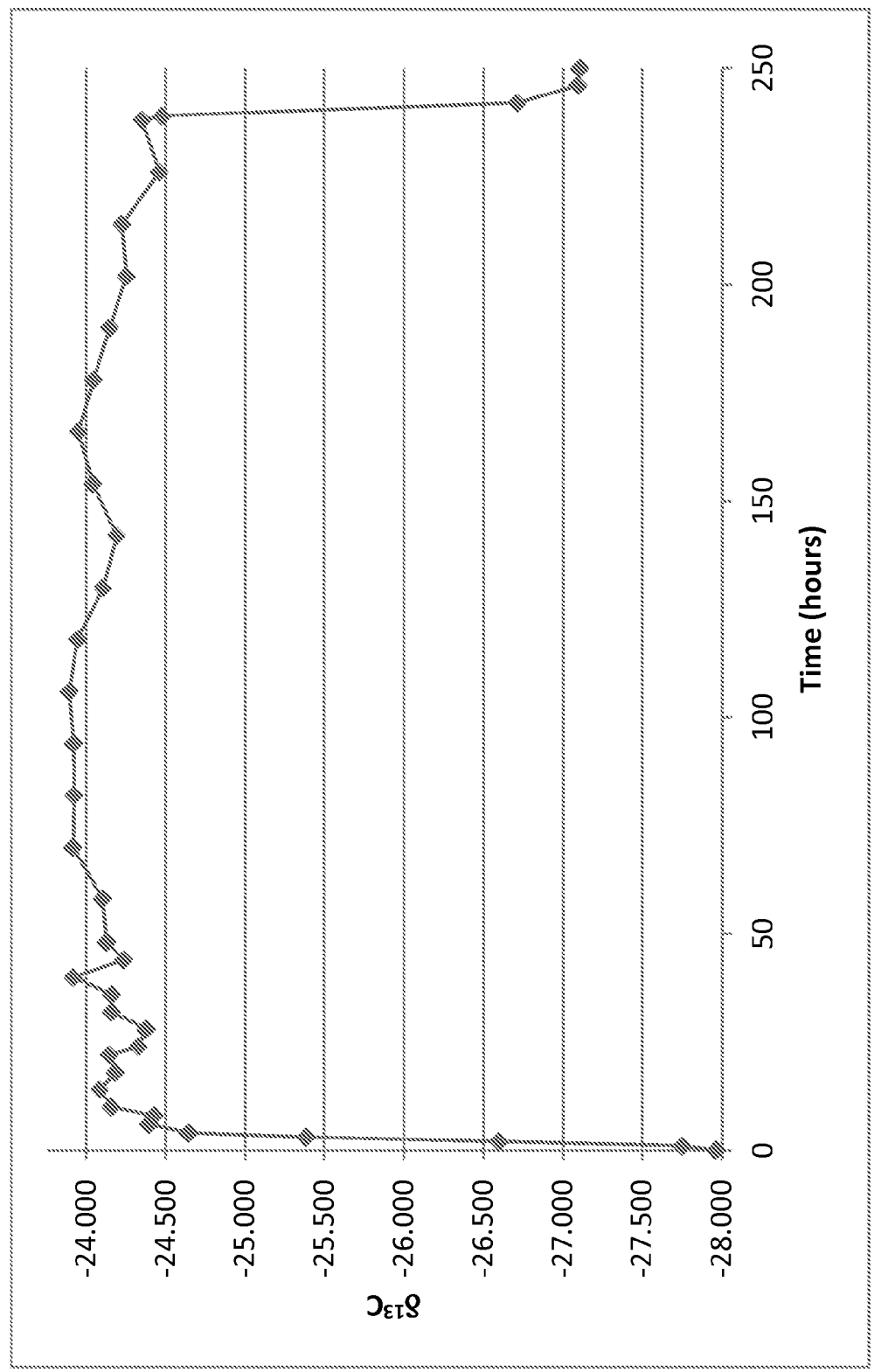
FIG. 7 illustrates the iTOC-CRDS-measured $\delta^{13}C$ PET resin values over time for a production run of petro-based amorphous PET resin conversion to renewable bio-source back to petro-based.
Figure 8:
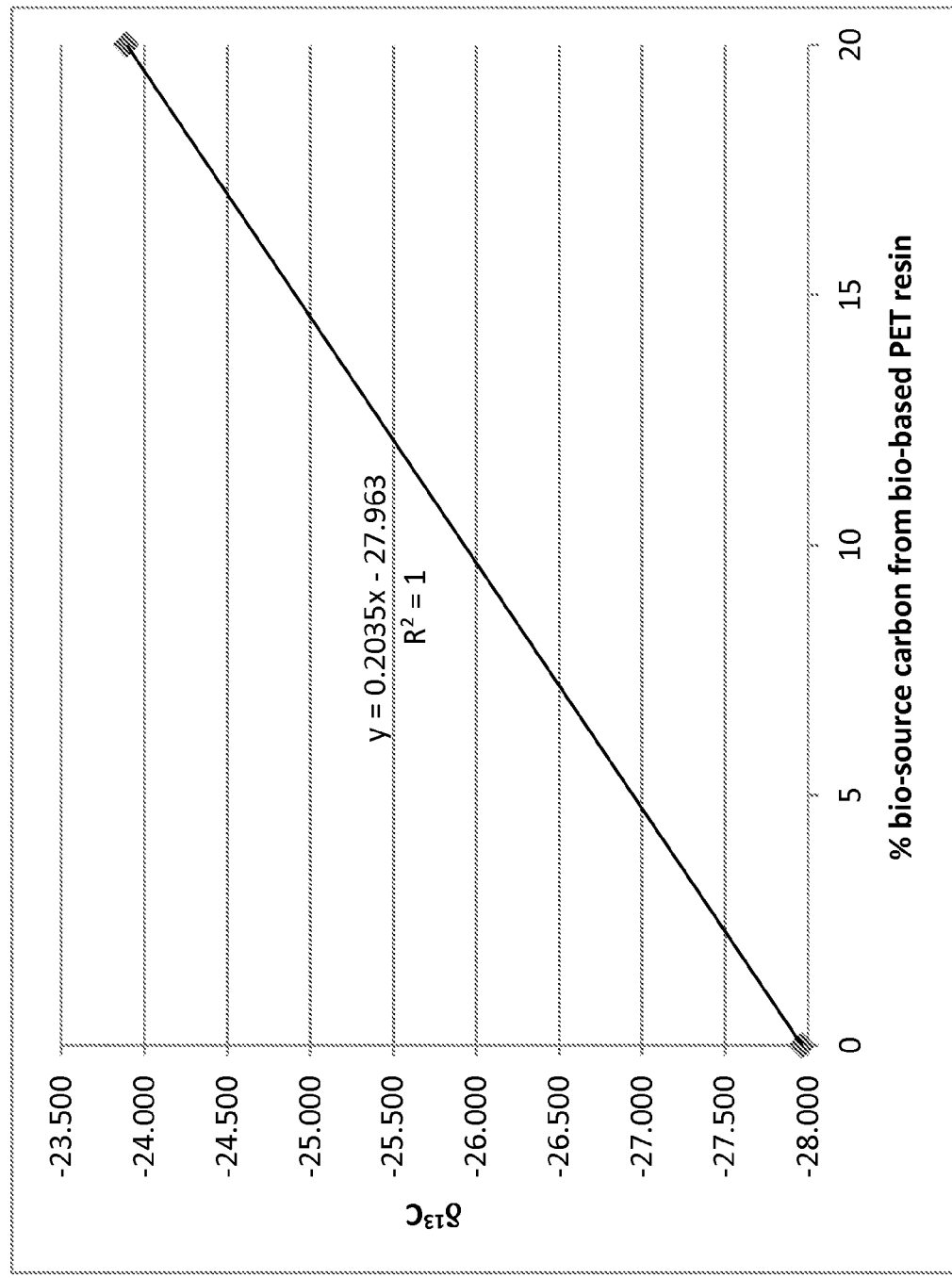
FIG. 8 illustrates the linear correlation plot of iTOC-CRDS-measured. $\delta^{13}C$ values versus AMS-measured renewable bio-source carbon values for the amorphous PET resin production run in FIG. 7.

Example 5—Measurement of δ³C Values and Calculated Renewable Bio-Source Carbon in MEG from Renewable Bio-Source in PET Resin Using iTOC-CRDS Table 6 shows the iTOC-CRDS measured $\delta^{13}C$ values and the calculated renewable bio-source carbon content values for amorphous PET resins over time for the production run in FIG. 7. Percent renewable bio-source carbon values are calculated using the linear trend line equation in FIG. 8. Percent renewable bio-source content of MEG in PET resin is calculated by multiplying the conversion factor (1.5625) with renewable bio-source carbon values.

Weight percentage from renewable bio-source in PET resin: [(molar mass or molecular weight from renewable bio-source of a PET repeat unit)/(molecular weight of a PET repeat unit)×100]. Percentage of carbon from renewable bio-source in PET resin: [(number of carbons from renewable bio-source)/(total number of carbons in PET resin)× 100].

Factor converting percent carbon from renewable bio-source in PET to percent MEG from renewable bio-source in PET:

$$\text{Conversion factor} = \frac{31.25 \text{ wt \%}}{20\%} = 1.5625$$

Where,
31.25% (wt./wt.) is the percent weight derived from MEG in a PET repeat unit since MEG contributes 60 g/mol out of the 192 g/mol per repeat unit of PET.
20% is the percentage of carbon derived from MEG in a PET repeat unit since MEG delivers 2 carbons out of the 10 carbons per repeat unit of PET.

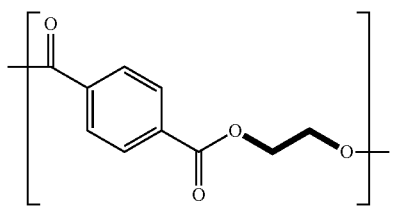

Chemical Structure of PET Resin

TABLE 6 iTOC-CRDS measured $\delta^{13}C$ values and calculated renewable bio-source carbon content values for amorphous PET resins over time for the production run in FIG. 7.

| Time (hours) | δ¹³C (Average) | % carbon from renewable bio-source in PET resin (Correlation Plot) | % MEG from renewable bio-source in PET resin (×1.5625 Conversion Factor) |
|---|---|---|---|
| 0 | −27.963 | 0 | 0 |
| 1 | −27.754 | 1 | 2 |
| 2 | −26.599 | 7 | 10 |
| 3 | −25.383 | 13 | 20 |
| 4 | −24.645 | 16 | 25 |
| 6 | −24.395 | 18 | 27 |
| 8 | −24.429 | 17 | 27 |
| 10 | −24.160 | 19 | 29 |
| 14 | −24.087 | 19 | 30 |

TABLE 6-continued iTOC-CRDS measured $\delta^{13}C$ values and calculated renewable bio-source carbon content values for amorphous PET resins over time for the production run in FIG. 7.

| Time (hours) | δ¹³C (Average) | % carbon from renewable bio-source in PET resin (Correlation Plot) | % MEG from renewable bio-source in PET resin (×1.5625 Conversion Factor) |
|---|---|---|---|
| 18 | −24.187 | 19 | 29 |
| 22 | −24.147 | 19 | 29 |
| 24 | −24.331 | 18 | 28 |
| 28 | −24.379 | 18 | 27 |
| 32 | −24.162 | 19 | 29 |
| 36 | −24.162 | 19 | 29 |
| 40 | −23.921 | 20 | 31 |
| 44 | −24.237 | 18 | 29 |
| 48 | −24.129 | 19 | 29 |
| 58 | −24.103 | 19 | 30 |
| 70 | −23.918 | 20 | 31 |
| 82 | −23.925 | 20 | 31 |
| 94 | −23.922 | 20 | 31 |
| 106 | −23.893 | 20 | 31 |
| 118 | −23.946 | 20 | 31 |
| 130 | −24.108 | 19 | 30 |
| 142 | −24.192 | 19 | 29 |
| 154 | −24.044 | 19 | 30 |
| 166 | −23.952 | 20 | 31 |
| 178 | −24.048 | 19 | 30 |
| 190 | −24.148 | 19 | 29 |
| 202 | −24.255 | 18 | 28 |
| 214 | −24.227 | 18 | 29 |
| 226 | −24.461 | 17 | 27 |
| 238 | −24.351 | 18 | 28 |
| 239 | −24.480 | 17 | 27 |
| 242 | −26.712 | 6 | 10 |
| 246 | −27.095 | 4 | 7 |
| 250 | −27.107 | 4 | 7 |

Figure 9:
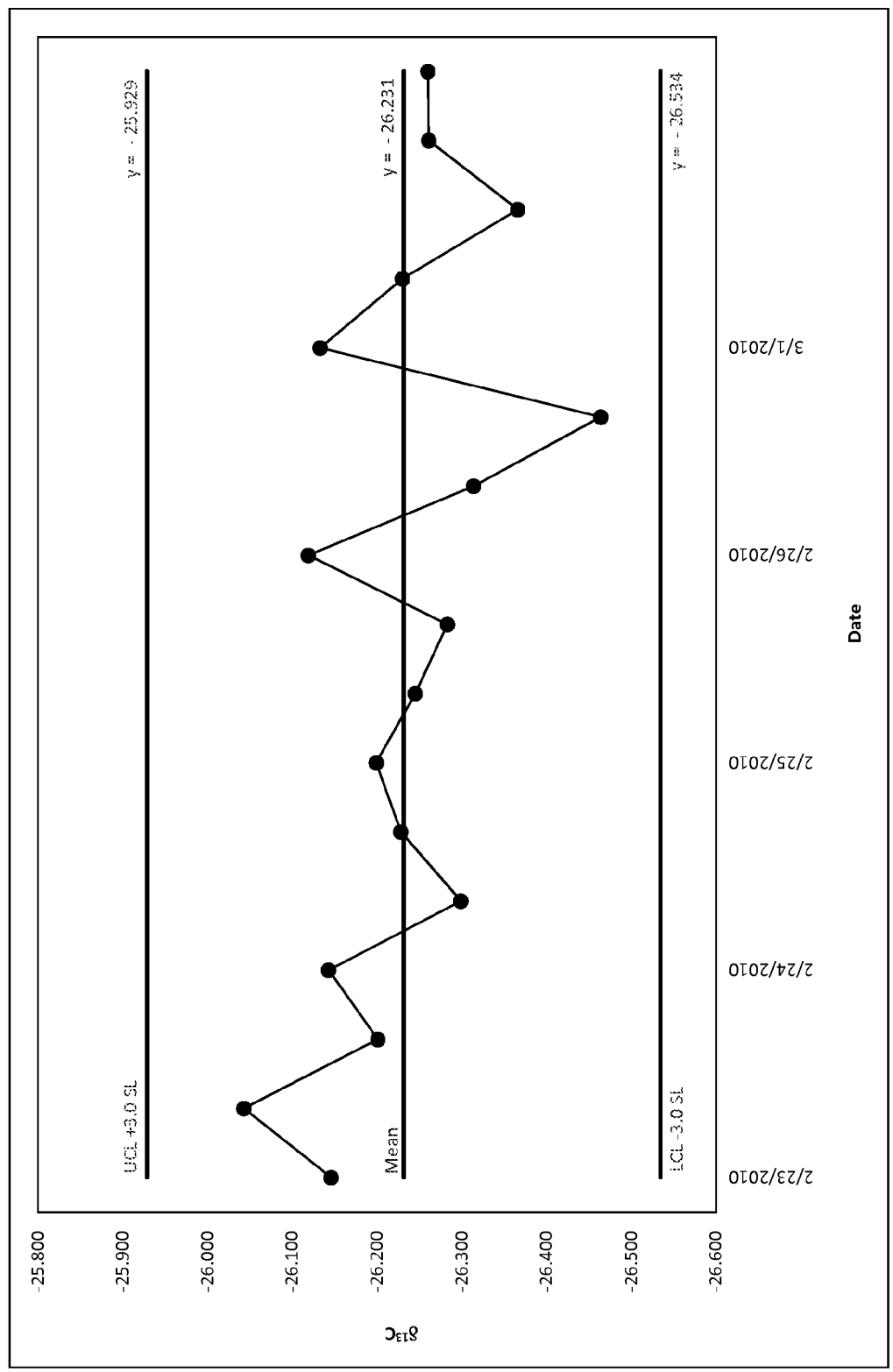
FIG. 9 illustrates a quality control chart for a PET resin sample measured over one week using iTOC-CRDS.
Figure 10:
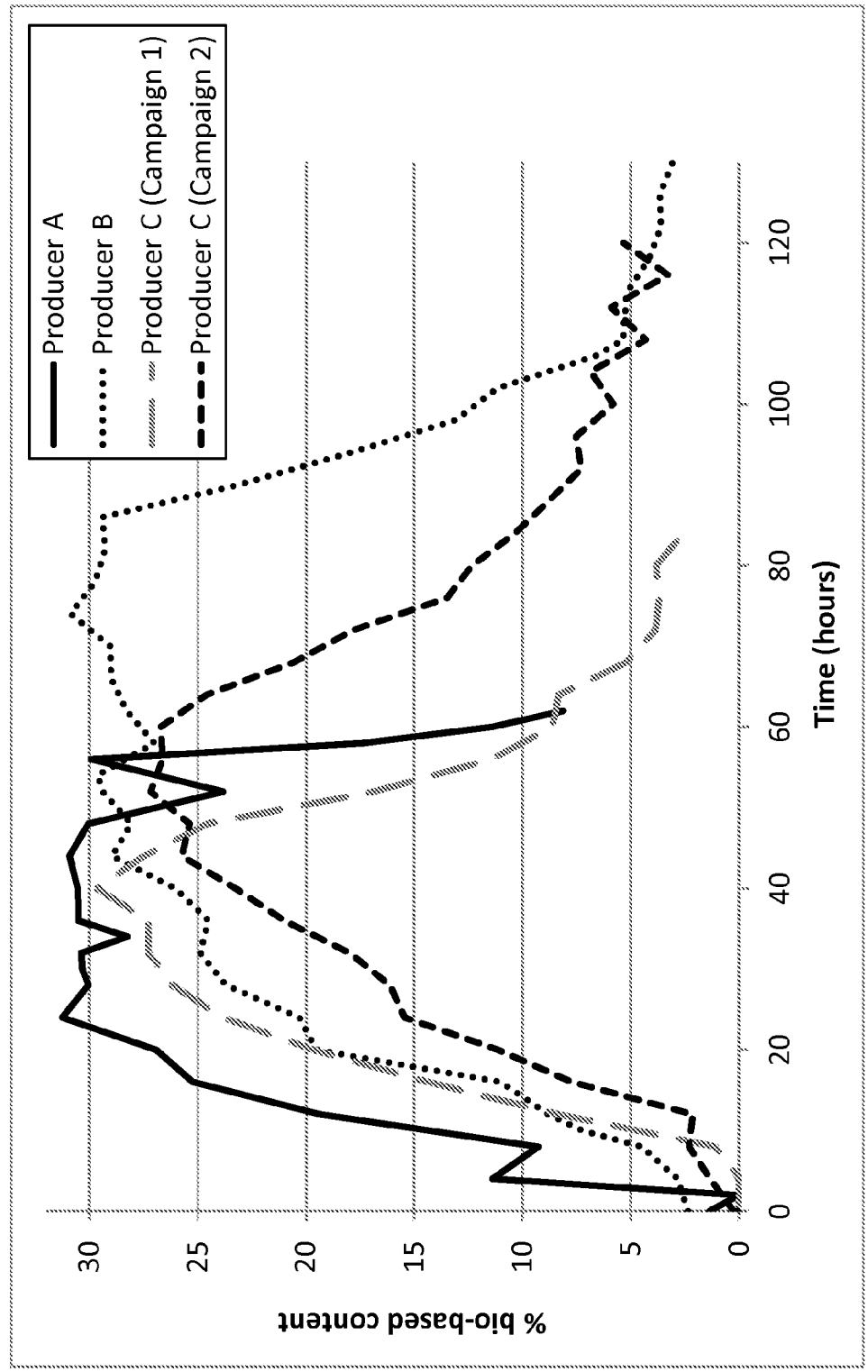
FIG. 10 illustrates renewable bio-content in renewable bio-based amorphous PET resin production at various resin producers over time.
Figure 11:
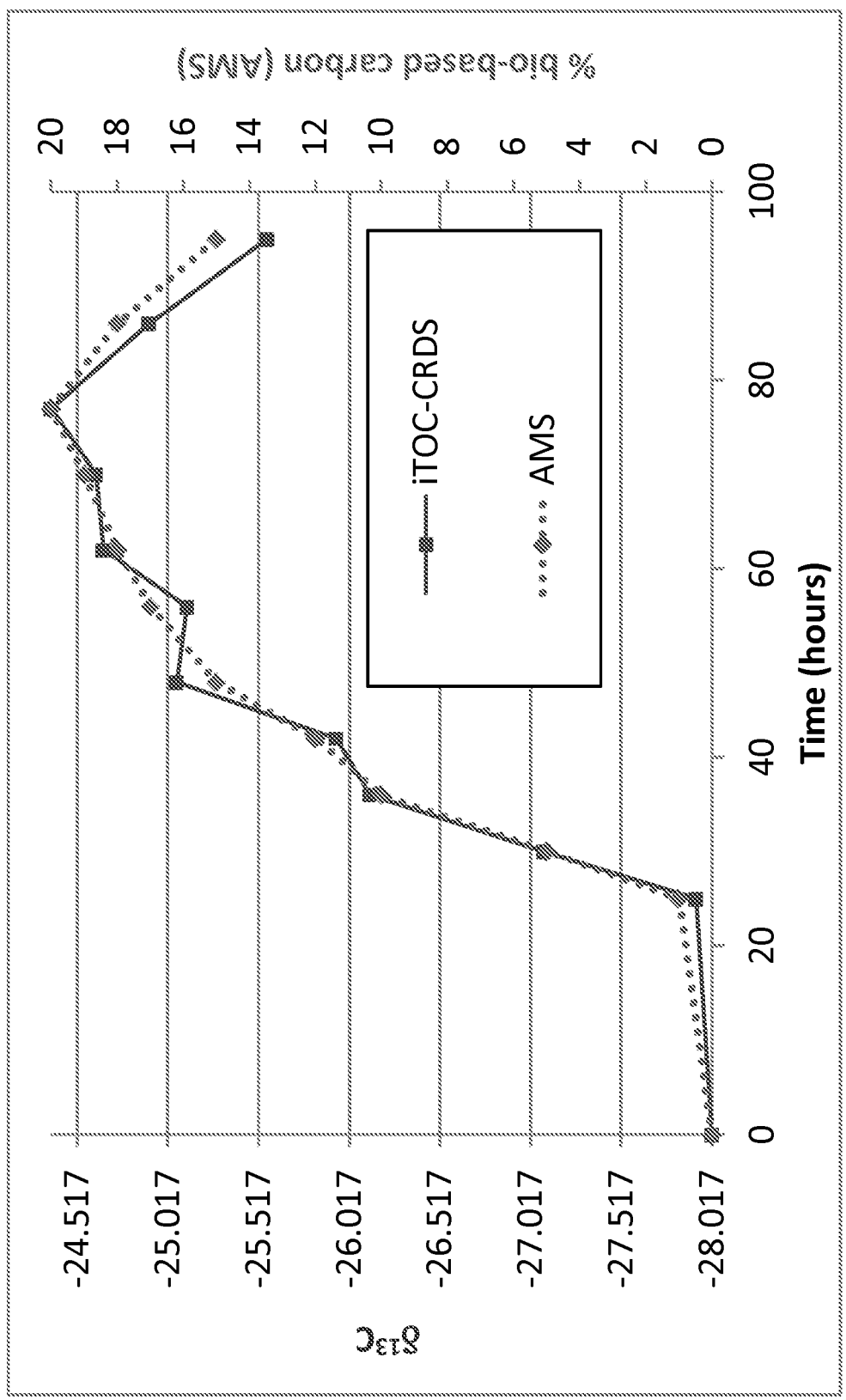
FIG. 11 illustrates iTOC-CRDS-measured, $\delta^{13}C$ values and AMS-measured renewable bio-source carbon content in a production run of a renewable bio-based PET resin.
Figure 12:
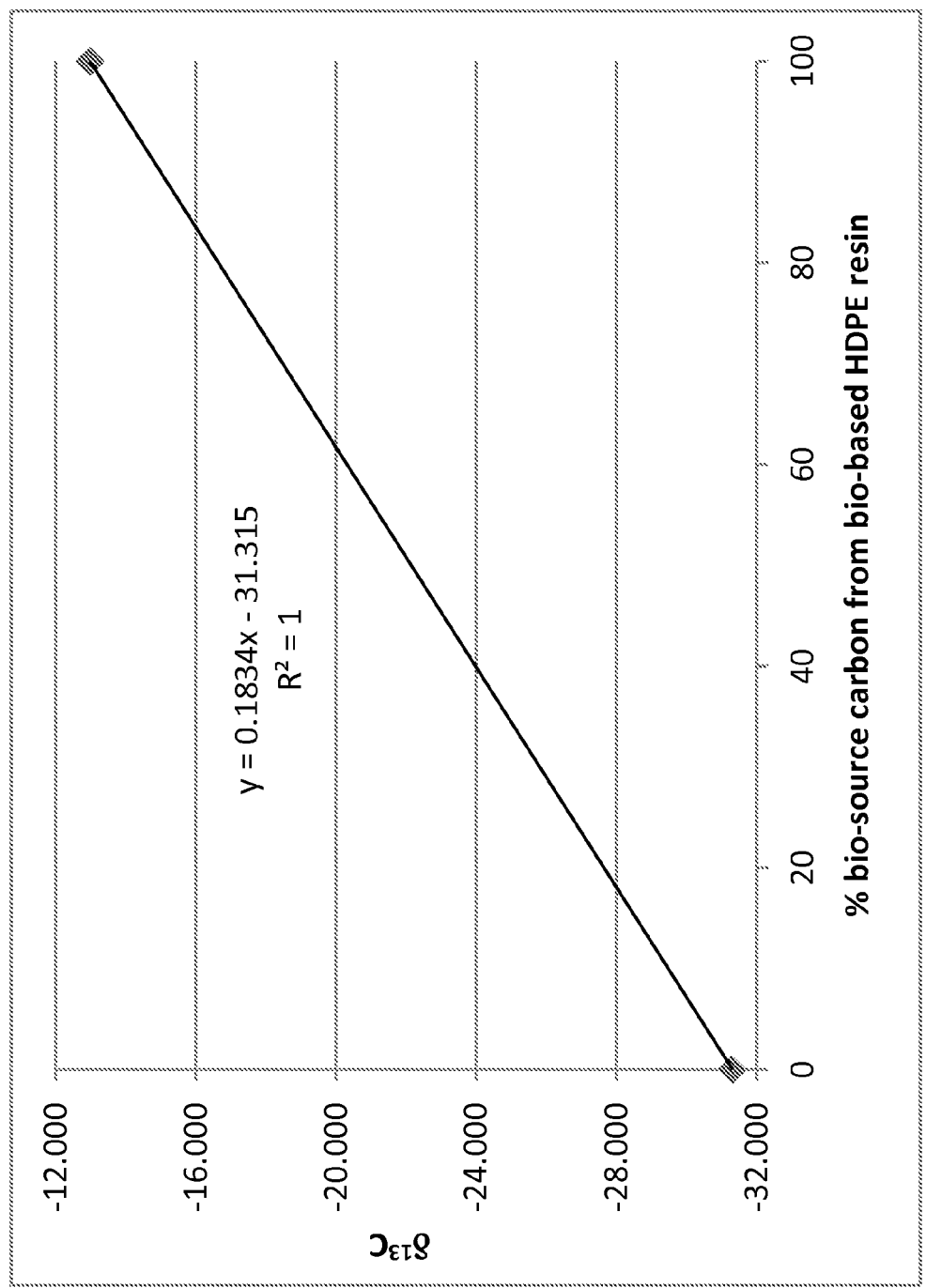
FIG. 12 illustrates the linear correlation plot of iTOC-CRDS-measured. $\delta^{13}C$ values versus AMS-measured renewable bio-source carbon values for bio-based HDPE resin production.

Example 6—Measurement Stability of MEG from Renewable Bio-Source in PET Resin Using iTOC-CRDS A quality control chart for a SSP PET resin sample measured over one week using the iTOC-CRDS (FIG. 9). The upper and lower control limits were set to three times the standard deviation. Over one week the instrument shows good stability. To avoid any variability within $\delta^{13}C$ measurements from CRDS detector drift, a set of production samples was analyzed within the same week. A control MEG or PET resin sample was analyzed with each daily sequence to monitor the $\delta^{13}C$ response. For comparing $\delta^{13}C$ data for a set of production MEG or PET resin samples from the same sources as a previous set of samples where the $\delta^{13}C$ data was acquired more than a week prior, the control sample was used to apply a $\delta^{13}C$ offset correction to the subsequent data.

Example 7—Measurement of Renewable Bio-Source Carbon Using CM-CRDS

Chemicals, Reagents, and Devices

Methanol.

Dewar filled with liquid nitrogen.

Retsch CryoMill equipped with 50 mL stainless steel (SS) jar and 25 mm SS grinding ball.

Ohaus Explorer E1D120 Analytical Balance (Max 4100 g).
Mettler Toledo XP6 Microbalance (Max 6.1 g) equipped with cleaning brush.
Costech Combustion Module.
Picarro Liaison interface module.
Picarro Cavity Ring Down Spectrometer—Isotopic $CO_2$ G1111-i.
Omega FMA 5510 mass flow controller connected to rear of Liaison for controlling $N_2$ flow rate.
Agilent Technologies ADM1000 Universal Gas Flowmeter
Ultra High Purity Nitrogen—outlet pressure 30 psi.
Ultra High Purity Oxygen—outlet pressure 30 psi.
Laboratory Air for Autosampler Pneumatics—outlet pressure 110 psi.
Compressed air.
Pressed tin capsules (4×6 mm).
SS tweezers.
gSource curette excavator #57-1 single ended without hole 1.5 mm.
Al tray for holding prepared tin capsules.
Small brush.
Funnel.
Hamilton gas tight syringe—10 µL.
Trace Clean Clear Borosilicate Glass Vials—20 mL with PTFE-faced Septa in Open Top Cap Precleaned (VWR Cat No.: 89093-854).
GC auto-sampler vial caps—National Scientific DP (dual purpose) blue polypropylene with ivory PTFE/red rubber septa (National No.: C4000-51B, VWR Cat. No.: 66030-008).

Cautions

Cross contaminations of other substances can occur. Use caution when handling tin capsules.

Standard Preparation

Monoethylene Glycol (100% Petro-Based and 100% Bio-Source):

Approximately 2 mL of each standard/sample was certified by an external laboratory, such as Beta Analytic (Miami, Fla.), for actual renewable bio-source content determination of radiocarbon ($^{14}C$) by ASTM method 6866-08a using Accelerator Mass Spectrometry (AMS).

PET Resin (100% Petro-Based and Highest Bio-Source Produced from bMEG):

Using the large capacity analytical balance, the weight of the 50 mL SS jar with grinding ball was tared. Approximately 5 g of resin was weighed in the jar. The jar was milled in a CryoMill with the following milling parameters:

| | |
|---|---|
| Pre-Cooling Frequency | 5.0 Hz |
| Pre-Cooling Cryo Cycles | 1 |
| Pre-Cooling Time | 5.0 min |
| Grinding Frequency | 25.0 Hz |
| Grinding Cryo Cycles | 1 |
| Grinding Time | 2.5 min |

The ground resin was collected into a 20-mL glass vial using a funnel and brush. A few grams of each ground resin was sent to an external laboratory for renewable bio-source content determination of radiocarbon ($^{14}C$) by ASTM method 6866-08a using Accelerator Mass Spectrometry (AMS).

The sample with the highest renewable bio-source content was measured initially using the CM-CRDS. The samples and standards were from the same sources to ensure reliable results.

MEG Sample Preparation

A 10-µL syringe was cleaned with methanol. The syringe was dried using compressed air. Using the syringe, 1 µL of the MEG was dispensed into a tin capsule. Using SS tweezers, the tin capsule was sealed by crimping and folding the tin. Using SS tweezers, the tin capsule was placed in the autosampler tray to be analyzed. The same MEG samples submitted to the external laboratory were analyzed in triplicate. These two samples were used to correlate relative $\delta^{13}C$ values to absolute renewable bio-source carbon values. A minimum of two points are required to bracket the $\delta^{13}C$ responses and percent bio-source carbon values.

Note: Data from the first and second run of the day should be omitted.

PET Resin Preparation

SS tweezers were used to place the tin capsule on the microbalance and tare the weight. A SS curette excavator was used to place approximately 1 mg (±0.1 mg) of the ground PET resin into the tin capsule. Using SS tweezers, the tin capsule was sealed by crimping and folding the tin. Using SS tweezers, the tin capsule was placed in the autosampler tray to be analyzed. The 100% petro-based sample and subsequent samples were analyzed in triplicate until the highest renewable bio-source content sample was identified. The two samples (100% petro-based and highest renewable bio-source produced) were submitted to an external laboratory for bio-source carbon content determination. These two samples were used to correlate relative $\delta^{13}C$ values to absolute renewable percent bio-source carbon values.

| CM-CRDS Instrument Parameters | |
|---|---|
| Furnace temperature | 980° C. |
| Sample delay | 18 sec |
| Sample stop | 40 sec |
| Oxygen stop | 50 sec |
| Run time | 400 sec |
| Oxygen loop | micro |
| Autosampler purge $N_2$ flow rate | 100 mL/min |
| CM $O_2$ flow rate | 30-35 mL/min |
| CM Carrier $N_2$ flow rate | 80 mL/min |
| Liaison gas bag purge $N_2$ flow rate | 75 mL/min |

Preparation of CM-CRDS

Placed system in Work mode.

Placed system in Remote mode.

Checked autosampler $N_2$ purge, CM $O_2$, and CM Carrier $N_2$ flow rates using electronic gas flowmeter.

Performed weekly CRDS detector internal calibration by allowing the CRDS to sniff atmospheric $CO_2$ for 30 min.

Analyzed a control PET resin sample daily to adjust necessary $\delta^{13}C$ offset due to CRDS detector drift.

Example 8—Precision of $\delta^{13}C$ Measurements of PET Resin and MEG Using iTOC-CRDS and CM-CRDS Table 7 shows a comparison of the average standard deviation of measured $\delta^{13}C$ values for PET resin and MEG samples acquired using iTOC-CRDS and CM-CRDS.

TABLE 7

Comparison of the average standard deviation of measured
$\delta^{13}C$ values for PET resin and MEG samples
acquired using iTOC-CRDS and CM-CRDS.

|  | iTOC-CRDS | CM-CRDS |
|---|---|---|
| No. Samples | 405 | 477 |
| No. Measurements | 1215 | 1431 |
| Measurement Period | 10 months | 6 months |
| Avg. Std. Dev. $\delta^{13}C$ | 0.121 ‰ | 0.109 ‰ |

We claim:

1. A method for measuring the renewable bio-content in renewable bioplastic resin during a production run comprising:
   a.) obtaining at least three resin samples during the production run, wherein each resin sample is obtained a different time point;
   b.) measuring $\delta^{13}C$ values of the at least three resin samples;
   c.) determining the actual renewable bio-source carbon content of two of the at least three resin samples in step b.) with the lowest and the highest $\delta^{13}C$ value;
   d.) determining the correlation between the two actual renewable bio-source carbon content determined in step c.) and the corresponding $\delta^{13}C$ values of the two samples;
   e.) determining the renewable bio-source carbon content of the remaining resin sample(s) obtained in step a.) based on said correlation and the measured $\delta^{13}C$ values of the remaining resin sample(s); and
   f.) calculating the renewable bio-content of the renewable bioplastic resin sample(s) from the renewable bio-source carbon content determined in step e.), wherein the production run occurs in a production facility transitioning from i) at least one non-renewable petroleum-derived monomer to at least one renewable bio-derived monomer; or ii) at least one renewable bio-derived monomer to at least one non-renewable petroleum-derived monomer.

2. A method for measuring the renewable bio-source carbon content in renewable bioplastic resin during a production run comprising:
   a.) obtaining at least three resin samples during the production run, wherein each resin sample is obtained at a different time point;
   b.) measuring $\delta^{13}C$ values of at least two resin samples;
   c.) determining the actual renewable bio-source carbon content of the at least two resin samples in step b.) with the lowest and the highest δ13C value;
   d.) determining the correlation between the at least two $\delta^{13}C$ values measured in step b.) with the corresponding actual renewable bio-source carbon content determined in step c.); and
   e.) determining the renewable bio-source carbon content of any remaining resin sample(s) obtained in step a.) based on said correlation and the measured $\delta^{13}C$ values of the remaining resin sample(s); wherein the production run occurs in a production facility transitioning from i) at least one non-renewable petroleum-derived monomer to at least one renewable bio-derived monomer; or ii) at least one renewable bio-derived monomer to at least one non-renewable petroleum-derived monomer.

3. The method of claim 1, wherein the $\delta^{13}C$ values are measured by Cavity Ring-Down Spectrometry (CRDS).

4. The method of claim 1, wherein the actual renewable bio-source carbon content is determined by Accelerator Mass Spectrometry (AMS) or Liquid Scintillation Counting (LSC).

5. The method of claim 1, wherein the correlation in step d.) is determined by linear regression of a plot of $\delta^{13}C$ versus actual renewable bio-based carbon content.

6. The method of claim 1 or 2, wherein the renewable bioplastic resin samples obtained include samples that are taken at time points prior to the transition and after the transition.

7. The method of claim 1 or 2, wherein the at least one renewable bio-derived monomer is renewable bio-MEG, renewable bio-derived TA or both.

8. The method of claim 1 or 2, wherein the renewable bio-derived monomer is from a single source and wherein the non-renewable petroleum-derived monomer is from a single source.

9. The method of claim 1, wherein the renewable bio-content of the renewable bioplastic resin is calculated by multiplying the renewable bio-source carbon content by a conversion factor, said conversion factor comprising a ratio of (1) the relative weight ratio of the renewable bio-derived monomer to a polymeric unit of the renewable bioplastic resin and (2) the relative contribution of carbons in the polymeric unit that originate from the renewable bio-derived monomer.

10. The method of claim 1, wherein the bio-derived monomer is from one geography.

11. The method of claim 1, wherein the bio-derived monomer is from one-source.

* * * * *